(12) United States Patent
Tosi et al.

(10) Patent No.: US 7,807,171 B2
(45) Date of Patent: Oct. 5, 2010

(54) THERAPEUTIC VACCINE TARGETED AGAINST P-GLYCOPROTEIN 170 FOR INHIBITING MULTIDRUG RESISTANCE IN THE TREATMENT OF CANCERS

(75) Inventors: Pierre-Francois Tosi, Reims (FR); Claudie Madoulet, Reims (FR); Claude Nicolau, Newton, MA (US); David T. Hickman, Strasbourg Cedex (FR)

(73) Assignee: AC Immune SA, Lausanne (CH)

( * ) Notice: Subject to any disclaimer, the term of this patent is extended or adjusted under 35 U.S.C. 154(b) by 317 days.

(21) Appl. No.: 10/902,276

(22) Filed: Jul. 30, 2004

(65) Prior Publication Data

US 2005/0175615 A1 Aug. 11, 2005

Related U.S. Application Data

(63) Continuation of application No. PCT/EP2004/008330, filed on Jul. 25, 2004.

(30) Foreign Application Priority Data

Jul. 25, 2003 (FR) .................................. 03 09188

(51) Int. Cl.
*A61K 38/00* (2006.01)
(52) U.S. Cl. ..................... 424/185.1; 530/326; 530/327
(58) Field of Classification Search ............... 424/185.1
See application file for complete search history.

(56) References Cited

U.S. PATENT DOCUMENTS

2006/0233758 A1 10/2006 Tosi et al.
2007/0281006 A1 12/2007 Nicolau et al.

FOREIGN PATENT DOCUMENTS

WO  WO 94/10198        5/1994
WO  WO 94/10198 A1 *   5/1994
WO  WO 9410198 A1 *    5/1994

OTHER PUBLICATIONS

Tosi et al. (Biochemical and Biophysical Research Communications 1995; 212: 494-500).*
Bashir et al. (Virshows Arch. 1998; 432: 279-287).*
Candido, K. A. et al, "Local Administration of Dendritic Cells Inhibits Established Breast Tumor Growth: Implications for Apoptosis-inducing Agents", Cancer Research 61, Jan. 1, 2001, pp. 228-236.
Chen, C-J. et al, "Internal duplication and homology with bacterial transport proteins in the mdr1 (P-glycoprotein) gene from multidrug-resistant human cells", Cell 47(3), Nov. 7, 1986 pp. 381-389.
Deprez, B. et al, "Comparative efficiency of simple lipopeptide constructs for in vivo induction of virus-specific CTL", Vaccine, 1996, pp. 375-382, vol. 14, No. 5, Elsevier Science Ltd., Great Britain.
Endicott, J. A. et al, "The Biochemistry of P-Glycoprotein-Mediated Multidrug Resistance", Annu. Rev. Biochem. 58, 1989, pp. 137-171, Annual Reviews Inc.
Fries, L.F. et al, "Liposomal malaria vaccine in humans: A safe and potent adjuvant strategy", Proc. Natl. Acad. Sci. USA, vol. 89, Jan. 1992, pp. 358-362.
Juliano, R. L. et al, "A Surface Glycoprotein Modulating Drug Permeability in Chinese Hamster Ovary Cell Mutants", Biochimica et Biophysica Acta 455, 1976, pp. 152-162, Elsevier/North-Holland Biomedical Press.
Klohs, W.D.et al, <<Resistance to Anthrapyrazoles and Anthracyclines in Multidrug-resistant P388 Murine Leukemia Cells : Reversal by Calcium Blockers and Calmodulin Antagonists >>, Cancer Research 46, Sep. 1986, pp. 4352-4356.
Mechetner, E.B. et al, „Efficient inhibition of P-glycoprotein-mediated multidrug resistance with a monoclonal antibody, Proc. Natl. Acad. Sci. USA, vol. 89, Jul. 1992, pp. 5824-5828.
Miller, T. P. et al, "P-Glycoprotein Expression in Malignant Lymphoma and Reversal of Clinical Drug Resistance With Chemotherapy Plus High-Dose Verapamil", Journal of Clinical Oncology, vol. 9, No. 1, Jan. 1991, pp. 17-24.
Pierré, A. et al, "In vitro and in vivo circumvention of multidrug resistance by Servier 9788, a novel triazinoaminopiperidine derivative", Investigational New Drugs 10, 1992, pp. 137-148, Kluwer Academic Publishers, Netherlands.
Roberts, M.J. et al, "Chemistry for peptide and protein PEGylation", Advanced Drug Delivery Reviews 54, 2002, pp. 459-476, Elsevier Science B.V.
Schnolzer, M. et al, "Constructing Proteins by Dovetailing Unprotected Synthetic Peptides: Backbone-Engineered HIV Protease", Science, New Series, vol. 256, No. 5054, Apr. 10, 1992, pp. 221-225, American Association for the Advancement of Science.
Stöber, P. et al, "Synthesis of Characteristic Lipopeptides of the Human *N-Ras* Protein and their Evaluation as Possible Inhibitors of Protein Farnesyl Transferase", Bioorganic & Medicinal Chemistry, vol. 5, No. 1, 1997, pp. 75-83, Elsevier Science Ltd., Great Britain.
Stupp, R. et al, "Ventricular arrhythmia and torsade de pointe: Dose limiting toxicities of the MDR-modulator S9788 in a phase I trial", Annals of Oncology 9, 1998, pp. 1233-1242, Kluwer Academic Publishers, Netherlands.
Thiebault, F. et al, "Cellular localization of the multidrug-resistance gene product P-glycoprotein in normal human tissues", Proc. Natl. Acad. Sci. USA, vol. 84, Nov. 1987, pp. 7735-7738.
Tosi, P. et al, "Immune Response Against the Murine MDRI Protein Induced by Vaccination With Synthetic Lipopeptides in Liposomes", Biochemical and Biophysical Research Communications, vol. 212, No. 2, Jul. 17, 1995, pp. 494-500, Academic Press, Inc.
Tsuruo, T., "6. Circumvention of drug resistance with calcium channel blockers and monoclonal antibodies", in *Drug Resistance in Cancer Therapy*, 1989, p. 73-95, Ozols, R.F. (ed), Kluwer Academic Publishers.

(Continued)

*Primary Examiner*—Brandon J Fetterolf
(74) *Attorney, Agent, or Firm*—Joyce von Natzmer; Pequignot + Myers LLC

(57) ABSTRACT

The invention relates to an immunogenic composition which comprises, firstly, a carrier and, secondly, as antigenic structure, conjugates comprising all or part of the amino acid sequences of at least one peptide derived from an extracellular loop of the P-170 protein, each peptide being combined with several molecules of fatty acid containing a carbon chain of between C12 and C24 so as to allow, under suitable administration conditions, the induction of anti-P-170 antibodies.

The invention relates to said composition for defining means for treating multidrug resistances.

21 Claims, 8 Drawing Sheets

OTHER PUBLICATIONS

Van Der Bliek, A.M. et al, "Sequence of *mdr3* cDNA encoding a human P-glycoprotein", Gene 71, 1988, pp. 401-411, Elsevier Science Publishers B.V. (Biomedical Division).

Yang, J. et al, "Treatment of Multidrug Resistant (MDR1) Murine Leukemia with P-Glycoprotein Substrates Accelerates the Course of the Disease", Biochemical and Biophysical Research Communications 266, 1999, pp. 167-173, Academic Press.

U.S. Appl. No. 11/550,778, Tosi et al. unpublished.

* cited by examiner

THERAPEUTIC VACCINE TARGETED AGAINST P-GLYCOPROTEIN 170 FOR INHIBITING MULTIDRUG RESISTANCE IN THE TREATMENT OF CANCERS

This application is a continuation application of International Application No. PCT/EP2004/008330, filed Jul. 25, 2004, which claims the benefit to French application No. FR0309188, filed Jul. 25, 2003. The content of these applications is incorporated herein by reference in their entirety.

FIELD OF THE INVENTION

The present invention falls within the context of the search for and development of novel agents that are useful for treating multidrug resistance (pleiotropic resistance or multidrug resistance) which appears in certain patients during the treatment of cancers.

The invention recounts in particular agents which can be used to induce an immune response in patients suffering from multidrug resistance in the course of treatment for cancer, with the aim of reducing, or even reversing, this resistance. The invention also relates to such agents for preventing the appearance of multidrug resistance.

The invention relates, in this regard, to a composition comprising, firstly, a carrier and, secondly, conjugates formed by covalent bonding between a peptide region and molecules of fatty acid containing a carbon chain of between C12 and C24, said peptide portion being derived from at least one of the extracellular loops of the P-170 protein. This immunogenic composition, administered under suitable conditions, allows the induction of anti-P-170 antibodies.

The invention also relates to methods of immunization using the above compositions based on conjugates combined with a pharmaceutically acceptable carrier, for example liposomes. The invention relates in particular to methods of immunization the implementation of which precedes, is concomitant with or follows a step of chemotherapeutic treatment administered to a patient.

Finally, the invention relates to the use of the composition according to the invention, for the in vivo treatment of multidrug resistance appearing in a patient suffering from a cancer treated by means of anticancer medicaments or, where appropriate, for the prevention of such a multidrug resistance.

BACKGROUND OF THE INVENTION

The phenomenon of multidrug resistance (MDR) was demonstrated at the end of the 1970s on cancer cell lines rendered resistant to chemotherapeutic drugs, in particular drugs used for the treatment of cancers. Multidrug resistance is characterized by a pleiotropic resistance, with respect to chemotherapeutic drugs used for the treatment of a patient, when these drugs have different structures and specificities. Among the drugs capable of selecting or inducing pleiotropic resistance of the cancer cell, mention will be made of colchicine, adriamycin, actinomycin, vincristine, vinblastine and mitoxantrone. From a phenotypic point of view, multidrug resistance is characterized by a decrease in the intracellular accumulation of cytotoxic drugs, physiological modifications of the cell and overexpression in the cell membrane of P-glycoprotein, also called P-gp protein or alternatively P-170 protein (Van der Bliek et al. 1988. Gene 71(2): 401-411, Thiebaut et al. 1987 Proc. Natl. Acad. Sci. 84(21): 7735-7738, Endicott et al. 1989 Annu. Rev. Biochem. 58: 137-171). The P-170 protein is responsible for an active flux of medicaments out of the cell (also called active efflux), this phenomenon being dependant on ATP consumption. The recognition by the P-170 protein, and the P-170 protein-mediated excretion out of the treated cell, of a large variety of chemical compounds having diverse structures and functions remains one of the most enigmatic aspects of the function of this protein. The lack of demonstration of a common structural characteristic between the drugs which are the subject of cross resistance does not allow the development of drugs which would not be excreted, under the influence of P-170 protein, to be envisioned.

Multidrug resistance of tumors to chemotherapy agents constitutes a central problem in medical cancerology. While progress in support treatments are observed, the problem of drug resistance remains an obstacle to obtaining better cure rates. It is noted that the tumor cells may not respond to chemotherapy from the beginning of treatment. This de novo multidrug resistance is unfortunately common in several types of solid tumors. Moreover, it has been possible to observe a phenomenon of acquired resistance, which manifests itself in tumors which, at the beginning, responded to chemotherapy and which subsequently developed, in the more or less short term, resistance to treatments.

In order to be more effective, anticancer treatments have been combined with multidrug resistance-modulating agents, also called reverting agents, which can block the P-170 protein-mediated outflux of drugs out of the cell and thus circumvent multidrug resistance. The existing reverting agents, such as verapamil, quinine and cyclosporin, result in toxicity that is unacceptable for the patient when they are used at the doses required to inhibit the efflux activity of the P-170 protein. For example, verapamil rapidly showed its limits in the treatment of cancer reversion due to the appearance in the patient of dysfunctions such as hypotension, cardiac arrhythmia and congestive heart failure when it was administered at the curative dosage, which are also the limiting doses for toxicity (Miller et al. 1991. J Clin Oncol 9(1): 17-24).

More recent analogues, such as dexverapamil, PSC 833 (cyclosporin derivative) and, most recently, S9788 from Laboratoires Servier, have been the subject of clinical trials, the aim of which was to overcome multidrug resistance. However, these novel reverting agents experience limits for use that are comparable to those reported for the prior generation of reverting agents. In fact, the trials for treatment of multidrug resistance using S9788 (6-[4-[2,2-di-(4-fluorophenyl)ethylamino]-1-piperidinyl]-N,N'-di-2-propenyl-1,3,5-triazine-2,4-diamine), a triazineamino-piperidine derivative, have characterized the limits for use of this product, subsequent to the appearance of phenomena of cardiac toxicity, ventricular arrhythmia and torsade de pointe (Stupp et al. 1998. Ann Oncol 9(11): 1233-1242). Consequently, the multidrug resistance phenomenon is difficult to hold back with reverting agents, novel and conventional, due to treatment doses equivalent to the thresholds of toxicity for the patient who has become refractory to the chemotherapy.

Immunotherapy, in particular the use of monoclonal antibodies, has also been envisioned for treating multidrug resistance appearing in the patient. It was tested first for inhibiting the formation of tumors in ovarian cancer using the monoclonal antibody MRK16 (Tsuruo. 1989. Cancer Treat Res 48: 1811-1816). More recently, monoclonal immunotherapy in the treatment of multidrug resistance has been investigated more thoroughly by Mechetner and Roninson (1992. Proc Natl Acad Sci USA vol. 89 pp. 5824-5828). In fact, monoclonal antibodies UIC2 directed against an extracellular epitope of human P-glycoprotein were obtained and tested in vitro on cell lines resistant to anticancer agents. It was then shown that the inhibitory effect, in vitro, of the monoclonal antibodies UIC2 is comparable to that of verapamil used as maximum clinical doses (3 µM). The anti-P-170 monoclonal antibodies exert their effect by inhibiting the ATPase activity of the P-170 protein and by inhibiting the binding of medicinal products to the P-170 protein.

An appropriate immunotherapy, based on the injection of monoclonal antibodies into a patient, can have certain advantages insofar as it can eliminate the residual resistant cells of a tumor. However, the lack of knowledge of the specificity, of the toxicity, of the efficacy and of the mechanism of action of the antibodies limits the use of this approach for overcoming multidrug resistances due to the overexpression of the P-170 protein. In particular, the side effects related to the anti-mouse antibodies or anti-rabbit antibody immune reactions and the difficulties related to the lack of humanization of the monoclonal antibodies are not mastered in monoclonal immunotherapy.

SUMMARY OF THE INVENTION

The aim of the present invention is therefore to propose an alternative strategy to the already available treatments for multidrug resistance in cancer, for the purpose of remedying, at least partly, the disadvantages of known treatments for multidrug resistance. The invention proposes, in this respect, an immunotherapy based on the induction of polyclonal autoantibodies specific for P-glycoprotein (P-170 protein). This immunotherapy is obtained using the antigenic capacity of conjugates comprising peptides derived from at least one of the extracellular loops of the P-170 protein to induce antibodies in a patient when these peptides are presented and administered in a form which allows or promotes the expression of the antigenic capacity, and in particular when they are combined with a pharmaceutically acceptable carrier. In particular, the antibodies are autoantibodies induced against human P-170.

The invention therefore relates in particular to an immunogenic composition comprising, firstly, a carrier and, secondly, as antigenic structure, conjugates comprising all or part of the amino acid sequences of at least one peptide derived from an extracellular loop of the P-170 protein, each peptide being combined with at least two molecules of fatty acid containing a carbon chain of between C12 and C24, so as to allow, under suitable administration conditions, the induction of anti-P-170 antibodies.

The authors of the present invention have, surprisingly and unexpectedly, shown that a 77% increase in survival time in mice immunized with the immunogenic composition as described in the present invention and after inoculation of the cancer cells, followed by a chemotherapeutic treatment plane, is observed.

These results are very promising since the best published results obtained in the treatment of multidrug resistance is the same cancer model described a 49% increase in survival in mice treated with another substance (Pierré et al. 1992. Invest New Drug. 10: 137-148). In addition, Yang et al. (1999. BBRC. 266: 167-173) have observed, with the same cell line, only a 35% increase in the survival in mice treated with vincristine and cyclosporin A.

BRIEF DESCRIPTION OF THE DRAWINGS

The present invention is illustrated, without however being limited, by the following figures.

DESCRIPTION OF VARIOUS AND PREFERRED EMBODIMENTS OF THE INVENTION

Figure 1:
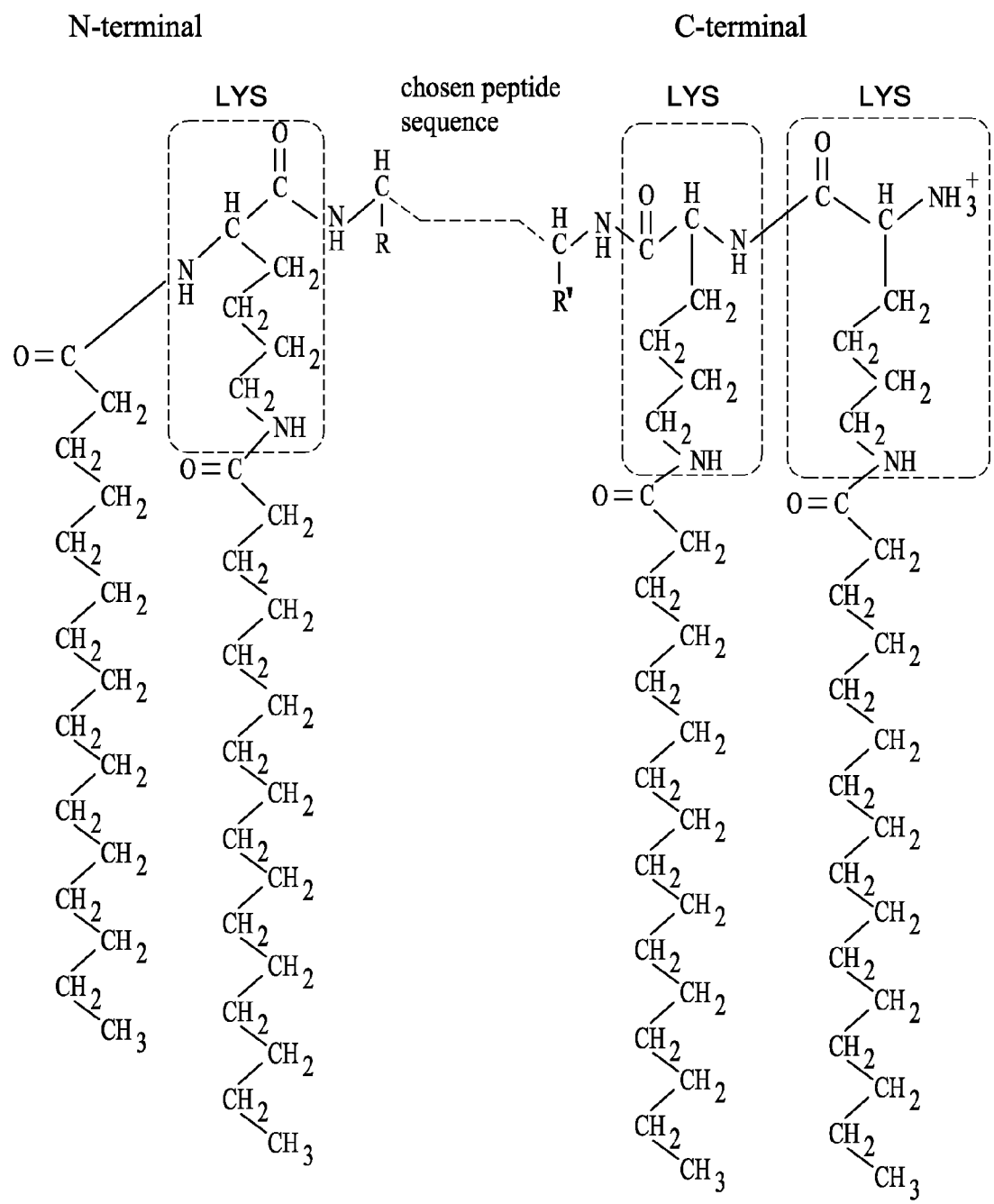
FIG. 1: Representation of the synthetic peptides corresponding to the extracellular fragments of the mouse P-170 protein, coupled to four molecules of palmitic acid (C16) per molecule of peptide.

P-Glycoprotein or P-170 protein is a 170 kDa membrane-bound phosphoglycoprotein identified by Juliano and Ling (1976. Biochim Biophys Acta 455(1): 152-162). The murine P-170 protein consists of 1276 amino acids forming two equivalent entities. The hydrophobic domains of the molecule are numbered from 1 to 12 and are involved in the outflux of chemotherapeutic drugs. Extracellular loops 1, 2 and 4 of the murine P-170 protein have been selected for their pronounced extracellular topology, suggesting that they may be antigenic in nature. In an equivalent manner, the human P-170 protein (Chen et al. 1986 Cell. 47(3): 381-389) is a 1280 amino acid protein consisting of two homologous domains each comprising six transmembrane helical domains and a nucleotide binding site. The hydrophobic regions of these transmembrane domains form extracellular loops considered to be the fragments for recognition of the P-170 protein from the outside of the cell. Extracellular loops 1, 4 and 6 of the human P-170 protein have also been selected as having a high antigenic capacity due to their particularly marked extracellular locations.

The immunotherapy used in the context of the invention adds to the cancer chemotherapy so as to allow the treating effects of the chemotherapeutic drugs to manifest themselves.

In accordance with the usual meaning in the context of the invention, "cancer" is defined by two main characteristics: cell growth and proliferation that is not regulated by external signals, and the ability to invade tissues along with, where appropriate, the ability to form metastases by colonizing distant sites.

These characteristics are the result of the intrinsic properties of cancer cells, i.e. of their caryotypic and genomic instability, of the uncontrolled proliferation, of their metastatic capacity accompanied by the acquisition of new phenotypes and also of the activation and derepression of oncogenes in said cancer cells. The term "cancer" is therefore understood to mean, in the context of the present invention, any phase of cell growth or proliferation having the above characteristics, evolving in particular toward the development of primary tumors and/or of metastatic tumors (secondary tumors).

In addition, for the purposes of the present invention, the expression "treatment for multidrug resistance" is understood to mean all the medical treatments intended to combat multidrug resistance so as to limit the consequences thereof, to avoid death and, preferably, to re-establish sensitivity to anticancer medicinal products. In this respect, the aim of the treatment for multidrug resistance is ideally directed toward curing the multidrug resistance, by inducing complete reversion to a chemotherapy-sensitive cell phenotype. This reversion may, however, be partial: consequently, the treatment of multidrug resistance will prove to be palliative, allowing prolonged remission of the patient. The treatment for multidrug resistance is also characterized by virtue of its prophylactic capacity making it possible to prevent the appearance of de novo or acquired multidrug resistances in the patient.

The invention therefore relates in particular to an immunogenic composition comprising, firstly, a carrier and, secondly, as antigenic structure, conjugates comprising all or part of the amino acid sequences of at least one peptide derived from an extracellular loop of the P-170 protein, each peptide being combined with at least two molecules of fatty acid containing a carbon chain of between C12 and C24, so as to allow, under suitable administration conditions, the induction of anti-P-170 antibodies.

In the context of the present invention, the immunogenic composition also allows the induction of anti-P-170 antibodies for the reversion of multidrug resistance appearing in a patient suffering from a cancer.

In a preferred embodiment, the conjugates comprise all or part of the amino acid sequences of at least two extracellular loops, preferably of at least three extracellular loops, of the P-170 protein.

The expression "conjugate" corresponds, according to the invention, to a reagent formed by covalent bonding between molecules of fatty acids containing a carbon chain of between C12 and C24, and amino acid sequences as described in the present invention, so as to form a lipid-peptide mixed molecule. The peptide sequence, obtained in particular by solid-phase synthesis, is covalently coupled to the fatty acid molecules constituting the lipid region of the molecule.

For the purposes of the present invention, the term "derived peptide" from the P-170 protein denotes all or part of the amino acid sequence making up each extracellular loop of the P-170 protein, as long as said "derived peptide" has at least one epitope of the extracellular loop from which it derives. A peptide derived from an extracellular loop advantageously has between 5 and 50 amino acid residues, preferably between 5 and 40, or between 10 and 30, advantageously between 10 and 25 residues. The following falls in a context of this definition: (1) peptides whose amino acid sequence is identical to the corresponding sequence of the extracellular loop from which they derive, or (2) peptides whose amino acid sequence is modified with respect to the sequence of the extracellular loop from which they derive, it being possible for said modification to consist of a point mutation by insertion, deletion or substitution, in particular conservative substitution, of one or more residues, provided that the peptide thus formed still carries an epitope of the P-170 protein. In particular, an acceptable mutation is a mutation which does not disturb the conformation of the modified peptide when it is included in the composition of the invention. This can be verified by means of the ability of the modified peptide to induce antibodies when it is formulated in a composition in accordance with the invention.

The peptides of the invention are preferably obtained by chemical synthesis, in particular using the methods described hereinafter.

In the context of the invention, the expression "extracellular loop" of P-glycoprotein (or P-170 protein) denotes each amino acid sequence of the P-170 protein having an extracellular topology or a significant connection with the extracellular environment so that it can be selected as a sequence carrying an epitope of this protein.

The amino acid sequences making up the synthetic peptides used in the context of the invention may be antigenic per se, or may be antigenic when they are presented in a conformation such that they conserve the conformation of the amino acid sequence which corresponds to them in the extracellular loop from which the peptide derives, or a conformation sufficiently similar to confer on the peptide formed an ability to induce the production of antibodies under suitable administration conditions. The ability to induce the production of antibodies may, for example, be verified in mice immunized with the peptides prepared in the context of the invention or by any other known means. Thus, the peptides of the invention advantageously have, in the immunogenic composition, a three-dimensional conformation such that they reproduce the conformation of the extracellular portion of loop from which the peptide derives, or such that it is similar to said conformation, so as to confer on the composition formed its immunogenic capacity. The appropriate presentation of the peptides advantageously results from their association with the other constituents of the immunogenic composition.

This ability to induce the production of antibodies is in particular obtained when the peptides of the invention are peptides that have been synthesized and modified so as to be in the form of conjugates, combined with a suitable carrier, in particular liposomes.

The conjugates according to the invention correspond to the antigenic structures carried by the carrier in the immunogenic composition. In the context of the invention, the expression "antigenic structure" denotes molecules capable of reacting with antibodies so as to form antigen/antibody complexes. Said "antigenic structure" of the immunogenic composition may or may not have, as such, the ability to induce a phenomenon of immunogenicity corresponding to the formation of antibodies specific for a given antigen.

By way of examples, these conjugates comprise peptides derived from extracellular loop 1 (mpp1) and from at least one of extracellular loops 2 (mpp2) or 4 (mpp4) of the murine P-170 protein, characterized by their sequence, their molecular mass and their purity after synthesis according to the experimental protocol described below in Table 1.

TABLE I

| Conjugate name | Amino acid sequence | Calculated molecular mass | Observed molecular mass | Purity (%) |
|---|---|---|---|---|
| mpp1 SEQ ID NO 1 | K-G-GNMTDSFTKAEASILPSITNQ SGPNSTLIISNSSLEEE-G-K-K-NH$_2$ | 5436 | 5437 | 91.6 |
| mpp2 SEQ ID NO 2 | K-G-KVLTSFTNKELQAYAK-G-K-K-NH$_2$ | 3293 | 3293 | 93.8 |
| mpp4 SEQ ID NO 3 | K-G-SRDDDMETKRQNEN-G-K-K-NH$_2$ | 3190 | 3188 | 95.3 |

The calculated and observed molecular masses of the peptides derived from extracellular loops 1, 2 and 4 of the murine P-170 protein were obtained by analysis by mass spectrometry, namely:

[M+H+] for the calculated molecular mass,

MALDI-TOF and PDMS-TOF for the measured molecular mass, i.e.

(Matrix Assisted Laser Desorption Ionization—Time of Flight)

(Plasma Desorption Mass Spectrometry—Time of Flight).

In addition, the amino acid sequences are also analyzed by hydrolysis of aliquots in 6N HCl/phenol at 110° C. in order to verify the expected and obtained number of amino acids (expected/obtained):

mpp 1, A (2/1.5), D (5/4.4), E (5/6.6), F (1/0.6), G (4/3.4), I (4/3.6), K (4/4.0), L(3/3.5), M (1/0.7), P (2/1.8), T (4/3.0), S (8/7.4).

mpp 2, A (2/2.3), D (1/1.2), E (2/2.4), F (1/1.0), G (2/2.1), K (6/6.0), L (2/2.1), S (1/0.9), V (1/1.0), Y (1/1.0).

mpp 4, D (5/5.0), E (3/3.1), G (2/2.0), K (4/3.7), S (1/0.9), R (2/1.9).

According to a particularly advantageous embodiment of the invention, the conjugates comprise peptides derived from extracellular loop 1 (hpp1) (hpp: human palmitoyl peptide) and from at least one of extracellular loops 4 (hpp4) and 6 (hpp6) of the human P-170 protein. The peptides of the conjugates therefore comprise amino acid sequences derived from extracellular loops 1 (hpp1) and 4 (hpp4) or from extracellular loops 1 (hpp1) and 6 (hpp6).

Preferably, the conjugates of the immunogenic composition comprise peptides derived from the three loops 1 (hpp1), 4 (hpp4) and 6 (hpp6) of the human P-170 protein.

Given the 47-amino acid length of loop 1 of the P-170 protein, peptides derived from this loop may result from said loop 1 being divided up into three fragments, obtained by cleavage at the glycosylation sites. The three derived peptides give rise to the following three conjugates hpp1a, hpp1b and hpp1c, the synthesis of which can be carried out. Other peptides may be fragments of these three peptides, containing one or more epitopes. Consequently, the conjugates according to the invention therefore comprise all or part of the peptides derived from extracellular loop 1 of the human P-170 protein corresponding to the three peptides resulting from cleavage of said loop 1 at the glycosylation sites.

The peptide sequence of the conjugates can be used as they are for preparing immunogenic compositions according to the invention, in particular in combination with liposomes.

The peptides of these conjugates are be chosen, respectively, from the following amino acid sequences:

for loop 1 (SEQ ID NO 4):
GEMTDIFANAGNLEDLLMSNITNRSDINDTGFFMNLE
EDMTRYAYYYS for loop 1a (SEQ ID NO 5):
GEMTDIFANAGNLEDLLMS for loop 1b (SEQ ID NO 6):
NITNRSDINDTGFF for loop 1c (SEQ ID NO 7):
MNLEEDMTRYAYYYS for loop 4 (SEQ ID NO 8):
FSRIIGVFTRIDDPETKRQNSNLFS for loop 4a (SEQ ID NO 9):
FTRIDDPETKRQNSNLFS for loop 6 (SEQ ID NO 10):
FRFGAYLVAHKLMSFED and/or a combination thereof.

and/or a combination thereof.

For extracellular loop 1, use will advantageously be made of the three peptides 1a, 1b and 1c in the same composition. Alternatively, peptides 1 a and 1 b or 1 a and 1 c or 1 b and 1 c will be used.

Table II recapitulates the amino acid sequences of the conjugates corresponding to extracellular loops 1, 4 and 6 of the human P-170 protein. The amino acid sequences corresponding to the sequences of the derived peptides are in large letters, while the small letters correspond to the added amino acids to which the fatty acid molecules are coupled.

The sequence, the molecular mass and the purity of the peptides described in Table II can be controlled by means of the techniques described above for the peptides of Table I.

A peptide derived from an extracellular loop advantageously has a purity equal to or greater than 90%, advantageously between 91% and 98%, measured by HPLC chromatography after synthesis.

TABLE II

| Conjugate name | Amino acid sequence from human P-170 human |
|---|---|
| Hpp1 (SEQ ID NO 11) | K-G-GEMTDIFANAGNLEDLLMSNITNRSDINDTGFFMNLE EDMTRYAYYYS-G-K-K-NH$_2$ |
| Hpp1a (SEQ ID NO 12) | K-G-GEMTDIFANAGNLEDLLMS-G-K-K-NH$_2$ |
| Hpp1b (SEQ ID NO 13) | K-G-NITNRSDINDTGFF-G-K-K-NH$_2$ |
| Hpp1c (SEQ ID NO 14) | K-G-MNLEEDMTRYAYYYS-G-K-K-NH$_2$ |
| Hpp4 (SEQ ID NO 15) | K-G-FSRIIGVFTRIDDPETKRQNSNLFS-G-K-K-NH$_2$ |
| Hpp4a (SEQ ID NO 16) | K-G-FTRIDDPETKRQNSNLFS-G-K-K-NH$_2$ |
| Hpp6 (SEQ ID NO 17) | K-G-FRFGAYLVAHKLMSFED-G-K-K-NH$_2$ |

In the context of the present invention, the amino acid sequences corresponding to the sequences of the extracellular loops (represented in large letters) can be extended, in particular at their end(s), by means of amino acid residues (represented in the peptides illustrated hereinafter in small uppercase letters) to which the fatty acid residues are coupled. Various conjugate sequences of the invention coupling amino acid sequences and fatty acid molecules are represented in this form in the tables which follow.

Advantageously, the molecules of fatty acid containing a C12, C13, C14, C15, C16, C17, C18, C19, C20, C21, C22, C23 or C24 carbon chain are preferably C16 palmitic acid molecules. The carbon chains of the fatty acid molecules of between C12 and C24 are linear or branched. Preferably, the fatty acid molecules have linear carbon chains. On the other hand, the fatty acid molecules may be neither monounsaturated nor polyunsaturated due to reaction incompatibility during the peptide synthesis, in particular during the final step of deprotection in the presence of strong acid.

Preferably, each conjugate comprises at least four molecules of fatty acid containing a carbon chain of between C12 and C24, the fatty acid molecules preferably also being distributed at the N- and C-terminal ends of the peptides. According to the fatty acids, other distributions may be envisioned, including within the amino acid sequence. These peptides are also coupled covalently to the fatty acid molecules.

Preferably, the peptides in the conjugates are each coupled to four molecules of palmitic acid; they are therefore tetrapalmitoylated.

Preferably, two molecules of palmitic acid are coupled to the N-terminal end and two molecules of palmitic acid are coupled to the C-terminal end of the peptide.

Preferably, and as illustrated in Table II, the amino acid sequences of the extracellular loops of the peptides of the conjugates are extended in the N- and/or C-terminal position by one or more amino acid residues, so as to allow combination with the molecules of fatty acid containing a carbon chain of between C12 and C24.

The combining of said peptides with said fatty acids may be carried out exclusively in the N-terminal position or, alternatively, exclusively in the C-terminal position. Advantageously, in the conjugates, the combining of the peptides with the fatty acids is carried out in the N-terminal and C-terminal position of the peptide sequences, in particular so as to give tetrapalmitoylated sequences.

Alternatively or cumulatively, it may be envisioned to combine fatty acids with internal residues in the peptide sequence.

The conjugates as defined in the present invention may also comprise, in addition, one or more PEG molecules.

The "pegylation", i.e. the process which consists in covalently coupling a PEG molecule to a peptide, so as to increase the immunogenicity/immunogenic nature of a peptide used as antigen, is a technique well known to those skilled in the art (2002. Adv Drug Deliv Rev. 54(4): 459-476).

This process makes it possible in particular to increase the accessibility of the peptide sequence and, in this way, the presentation of the antigen.

In general, the longer the peptide sequence, the greater the number of molecules of PEG.

Advantageously, the molecule(s) of PEG, from 1 to 8000, is (are) attached to the lysine (K) residues found in the N- and/or C-terminal position of the amino acid sequences of the extracellular loops of the peptides of the conjugates as described in the present invention. Each peptide is covalently attached to at least two molecules of fatty acid containing a carbon chain of between C12 and C24 or to at least two chains of polyethylene glycol (1-8000) which are each coupled to a molecule of phosphatidylethanolamine in order to make it possible to reconstitute these antigenic complexes in the lipid bilayer of the liposomes. Under suitable administration conditions, these antigens reconstitute, in adjuvant-liposomes, the induction of anti-P-170 antibodies.

In the context of the invention, the expression "carrier" of an immunogenic composition denotes any agent providing transport of the antigenic structures in the immune system. In particular, a carrier in accordance with the invention may consist of liposomes, of bacterial membrane proteins such as *Neissera meningitides* OMPCs or *Escherichia coli* TraT, of entobacterial Omp proteins, of nanoparticles, of micelles, of gold particles, of microbeads and of virosomes.

To form the immunogenic compositions of the invention from the abovementioned conjugates, liposomes are advantageously selected as carrier for preventing the conjugates in the composition of the present invention.

Advantageously, said conjugates are present at the surface of the liposomes.

For the purposes of the present invention, the term "liposomes" is understood to mean an artificial spherical particle consisting of one or more layers of phospholipids, ensuring presentation to the cells of the immune system of the peptides carrying the epitopes and derived from the extracellular loops of P-glycoprotein (P-170).

The composition according to the present invention advantageously comprises the conjugates and the liposomes in a molar ratio of between 1/10 and 1/1000, preferably between 1/50 and 1/500, advantageously in a molar ratio of 1/250.

Advantageously, the liposomes are prepared by mixing dimyristoylphosphatidylcholine (DPMC), dimyristoylphosphatidylglycerol (DMPG) and cholesterol in a molar ratio of, respectively, 0.9:0.1:0.7. The products used above are preferably of synthetic origin in order to avoid the possibilities of contamination with endotoxins, prions or viruses. For example, the DMPC and DMPG phospholipids are of synthetic origin (Avanti Polar Lipids USA) and the cholesterol, which is 98% pure, is of animal origin. Monophosphoryl lipid A (MPLA), also of synthetic origin, and known to increase the immune response (Fries et al. 1992. Proc Natl Acad Sci 89(1): 358-362) was added to liposomes, and tested, at a concentration of 40 μg per μmol of phospholipids.

The composition according to the present invention also comprises at least one adjuvant. The term "adjuvant" is used, in the context of the present invention, to denote a product which allows a nonspecific stimulus of the immune responses and which increases the antigenicity of the antigenic structures. The adjuvant would act by mobilizing the phagocytic cells to the site of deposition of the antigenic structures and ensuring a slower release of the antigens, which prolongs the stimulation of the immune system.

In particular, the adjuvants used in the present immunogenic composition are chosen from the group consisting of alum, calcium phosphate, interleukin 1, monophosphoryl lipid A (MPLA) and/or microcapsules of proteins and of polysaccharides. Advantageously, alum is the adjuvant used in the context of the present invention.

Such immunogenic compositions are prepared in the form of liquid solutions, or of injectable suspensions, or else in a solid form suitable for solubilization prior to injection in the context, for example, of a kit for making use of the present composition, as described below.

The invention also relates to peptides which are derived from at least one extracellular loop of the P-170 protein and which are the induction of anti-P-170 antibodies when they are used in the immunogenic compositions as described. These peptides are, respectively, chosen from the following amino acid sequences:

SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16 and SEQ ID NO 17.

Also included in the present invention are the nucleic acid, DNA or RNA, sequences encoding the peptides as described above.

The present invention relates not only to the immunogenic composition considered per se and defined above, but also to a method for preparing this composition.

The experimental results below show that the combining of specific peptides with only two molecules of palmitic acid may not result in the expression of an immunogenic response. This reflects the need to select the fatty acids so as to confer on the conjugates formed the conformation required for the induction of an immune response.

Particular attention is also given to the synthesis of the conjugates according to the invention, and in particular to their peptide region. In fact, the previous studies by Tosi et al. (1995) demonstrated that the peptide sequence of mpp1, which is the longest of the conjugates, with 43 amino acids, did not make it possible to obtain an immune response. In the absence of explanations or working hypotheses regarding this observation, the inventors have revealed, in the context of the present invention, the essential role of a very precise peptide synthesis. The inventors have therefore developed and shown that an improved method of synthesis allowing a more effective production of certain amino acids by avoiding their involvement in early terminating reactions makes it possible to obtain in particular an immunoreactive mpp1 sequence. The conjugates according to the invention can therefore be obtained in a suitable form for producing the immunogenic composition of the invention by means of a solid-support synthesis according to the Boc/benzyl strategy.

In the case in point, as described in the example section, the peptides corresponding to the sequences of extracellular loops 1, 2 and 4 of murine P-170 were therefore synthesized by means of an Applied Biosystems 430A peptide synthesizer using the tert-butyloxycarbonyl/benzyl or Boc/benzyl strategy and, in situ, activation with (N-[(1H-benzotriazol-1-yl) (dimethylamino)methylene]-N-methylmethanaminium hexafluorophosphate N-oxide.

The synthesis of the peptides can be carried out on a peptide synthesizer, for example an Applied Biosystem 430A synthesizer, using (13,14)-tert-butyloxycarbonyl/benzyl and, in situ, activation with (N-[(1H-benzotriazol-1-yl)(dimethylamino)methylene]-N-methylmethanaminium hexafluorophosphate N-oxide (Scholzer M. et al Science 1992, 256 (5054): 221-225).

According to this method, the synthesis of the conjugates is based on the synthesis of the amino acid sequences of the extracellular loops of the peptides of the conjugates on a solid support according to the Boc/benzyl strategy, and then extension in the N- and/or C-terminal position with one or more amino acid residues so as to allow combination with the molecules of the fatty acid containing a carbon chain of between C12 and C24, followed by a step consisting of deprotection of the amine functions of the N and C-terminal lysines in order to couple them with the fatty acids containing a carbon chain of between C12 and C24. The final step is cleavage with a strong acid, such as anhydrous hydrofluoric acid, of the conjugates synthesized on the solid support, such as a resin.

This improved method of synthesis allows a more effective production of certain amino acids by avoiding their involvement in early terminating reactions.

The combining of said peptides with the fatty acids can be carried out either in the N-terminal position or, alternatively, in the C-terminal position.

Advantageously, in the conjugates, the combining of the peptides with the fatty acids is carried out in the N-terminal and C-terminal position of the peptide sequences, in particular so as to give tetrapalmitoylated sequences.

Alternatively or cumulatively, it is possible to envision combining the fatty acids with internal residues in the peptide sequence.

Each peptide of the immunogenic composition can be combined with several molecules of fatty acid by means of one or more molecules of PEG.

The conjugates obtained are then presented at the surface of liposomes.

Optionally, once they have been synthesized, the conjugates are purified, for example by RP-HPLC or reverse-phase high performance liquid chromatography. This purification step is made delicate by the presence of a lipid chain, which results in a broadening of the chromatographic peaks and solubility problems. Isolation of the expected product, from the impurities formed, during the elongation of the peptide, can be difficult and can result in low yields. In addition, the purification may be difficult insofar as the fatty acid is located in the C-terminal position. In fact, in this case, the desired product, but also the impurities, carry the lipophilic portion responsible for the chromatographic difficulties. In addition, since this strategy involves, at the end of synthesis, a step of cleavage and of deprotection in strong medium, this treatment limits the choice of the lipophilic portion (Deprez et al. 1996. Vaccine 14(5): 375-382; Stöber et al. (1997) Bioorg. Med. Chem. 5(1): 75-83).

The presentation, at the surface of the liposomes, of the conjugates obtained is then obtained mechanically. Specifically, the conjugates mixed with the liposomes fit exactly into the phospholipid membrane of the liposomes by means of their lipid doubles chains.

The present invention also relates to the use of this composition in methods of immunization according to the invention.

The present invention therefore relates to a method of immunization comprising a first administration, in particular by injection, of the immunogenic composition according to the invention and a boost administration of said composition (or booster), for example of two successive injections. The boost injections, exposing the same antigen several times, induce a strong secondary immune response. The repeated exposure of peptides derived from the extracellular loops of the P-170 protein, to the immune system, induces immunological memory and also rapid subsequent secondary responses with a high antibody titer.

More particularly, in the present method of immunization, the injections in humans are carried out 1 month apart.

According to one embodiment, the immunization with the composition according to the invention can be carried out concomitantly with or preceding an anticancer treatment administered to a patient.

Preferably, the immunization precedes the chemotherapy treatment in order to prevent and anticipate the appearance of a multidrug resistance phenotype in the patient. This treatment plan will be preferred to immunization concomitant with the chemotherapeutic treatments when the diagnosis and evolution of the cancer allow the curative therapeutic treatment (chemotherapy) to be delayed by at least 30 days from the date of diagnosis. The late treatment of the cancer does not prevent the method of immunization with the composition of the present invention being used. In fact, combining the anticancer treatment and the immunization with said immunogenic composition at the same time nevertheless induces an immune response for the production of anti-P-170 autoantibodies having a curative or palliative effect on the appearance of the multidrug resistance phenotype. The curative effect of the immunization with the present composition is illustrated by a reversion of multidrug resistance phenotype. In the context of the invention, the expression "reversion" of the multidrug resistance phenotype denotes the change from a phenotype of multidrug resistance to a phenotype "sensitive to the chemotherapeutic treatments".

For the purpose of the present invention, the term "chemotherapy", "anticancer" or "chemotherapeutic drugs" is intended to mean any curative or palliative treatment of primary or secondary tumors based on cytotoxic agents. Chemotherapy generally requires several cycles of treatment.

In the context of a method of immunization preceding the chemotherapy treatment, the implementation of the first injection of the composition according to the present invention precedes the start of the chemotherapeutic treatment by at least 60 days, preferably 63 and 67 days.

The compositions according to the invention can be administered topically, systemically (orally, nasally and via other mucosal routes) and/or parenterally (intravenously, subcutaneously, intramuscularly or intraperitoneally) or by combination of these routes, and effectively induce a protective immune response against multidrug resistance. The composition is formulated so as to allow easy administration via the various pathways above. In particular, the choice of the secondary compounds (wetting agent, emulsifier or buffer) is dictated by the chosen mode of administration.

Advantageously, the immunization is carried out by means of intramuscular and intraperitoneal administration, respectively, in humans and in mice.

One of the subjects of the present invention also relates to the provision of an antibody, in particular an autoantibody, induced against human or murine P-170, which binds specifically to the peptides of the conjugates according to the invention.

This antibody may be a polyclonal or monoclonal antibody, selected from the group comprising the IgG1, IgG2 and IgG3 isotypes and an IgM. In particular the Ig2 antibody may be of the subtype 2a or 2b.

The present invention also relates to an immunogenic composition comprising, firstly, a carrier and, secondly, conjugates comprising at least one peptide derived from extracellular loop 1 of the P-170 protein allowing the induction of anti-mpp1 antibodies, each peptide being combined with several molecules of fatty acid containing a carbon chain of between C12 and C24, said conjugates exhibiting all or part of the conformation of extracellular loop 1 of the P-170 protein, for the reversion of multidrug resistance appearing in a patient suffering from a cancer.

This composition is particularly suitable for treatments of solid tumors expressing the MDR1 gene encoding the human P-170 protein.

The present invention also relates to the use of the immunogenic composition according to the invention, for producing a vaccine intended for the treatment and/or prevention of a multidrug resistance appearing in a patient suffering from a cancer. The cancer as envisioned will be a kidney cancer, liver cancer, colon cancer, cancer of the intestine, prostate cancer, breast cancer, bladder cancer, brain cancer, blood cancer (leukemia) and/or cancer of the medullary tissues (myeloma). It may also be a solid tumor expressing the MDR1 gene encoding the human P-170 protein. The use of the immunogenic composition may also be carried out in combination with an anticancer treatment.

In particular, it is envisioned, in clinical phases I/II, to use the present vaccine in patients bearing solid tumors, in particular cancers expressing the MDR1 gene encoding the human P-170 protein, such as kidney cancer, liver cancer, colon cancer, cancer of the intestine, prostate cancer, breast cancer, bladder cancer, brain cancer, blood cancer (leukemia) and/or cancer of the medullary tissues (myeloma). The patients chosen for this clinical study will be selected on criteria of non-immunodepression and of tolerance to a standard treatment. In parallel to these trials, a pharmacodynamic and tolerance study will be carried out in these same patients.

Finally, the composition according to the present invention will be used directly in patients spontaneously expressing multidrug resistance, in order to clinically evaluate in humans the rate of reversion of the multidrug resistance phenotype.

The present invention also comprises a method of treatment and/or prevention of a multidrug resistance appearing in a patient suffering from a cancer, in particular a cancer affecting the kidney, the liver, the colon, the intestine, the prostate, the breast, the bladder, the brain, the blood (leukemia) and/or the medullary tissues (myeloma), comprising the administration of the immunogenic composition as described.

The cancer particularly targeted by the treatment as described is a solid tumor expressing the MDR1 gene encoding the human P-170 protein.

Finally, a kit for making use of the immunogenic composition, comprising the immunogenic composition according to the invention and, optionally, reagents and/or instructions for use, is also envisioned.

EXAMPLES

I-1 Preparation of the Conjugates Formed by Covalent Bonding Between the Peptide Region and the Molecules of Fatty Acid Containing a Carbon Chain of Between C12 and C24

The synthesis of the peptides can be carried out at a peptide synthesizer, for example an Applied Biosystem 430A synthesizer, using (13,14)-tert-butyloxycarbonyl/benzyl and, in situ, activation with (N-[(1H-benzotriazol-1-yl)(dimethylamino)methylene]-N-methylmethanaminium hexafluorophosphate N-oxide (Scholzer M. et al. Science 1992, 256 (5054): 221-225), and they can then be coupled covalently with four molecules of palmitic acid per molecule of peptide (FIG. 1).

An improved method of synthesis allowing more effective production of certain amino acids by avoiding their involvement in early terminating reactions has been developed. This is particularly advantageous in the case of mpp1 due to its length (43 amino acids). The murine peptides mpp1, mpp2 and mpp4 were in particular synthesized and the results of the synthesis (analysis of the peptide sequence, molecular mass, and purity) were recorded in Table 1 above, each peptide having been controlled for its sequence by amino acid analysis after total acid hydrolysis, for its molecular mass by mass spectrometry analysis and for its purity by HPLC.

Figure 2:
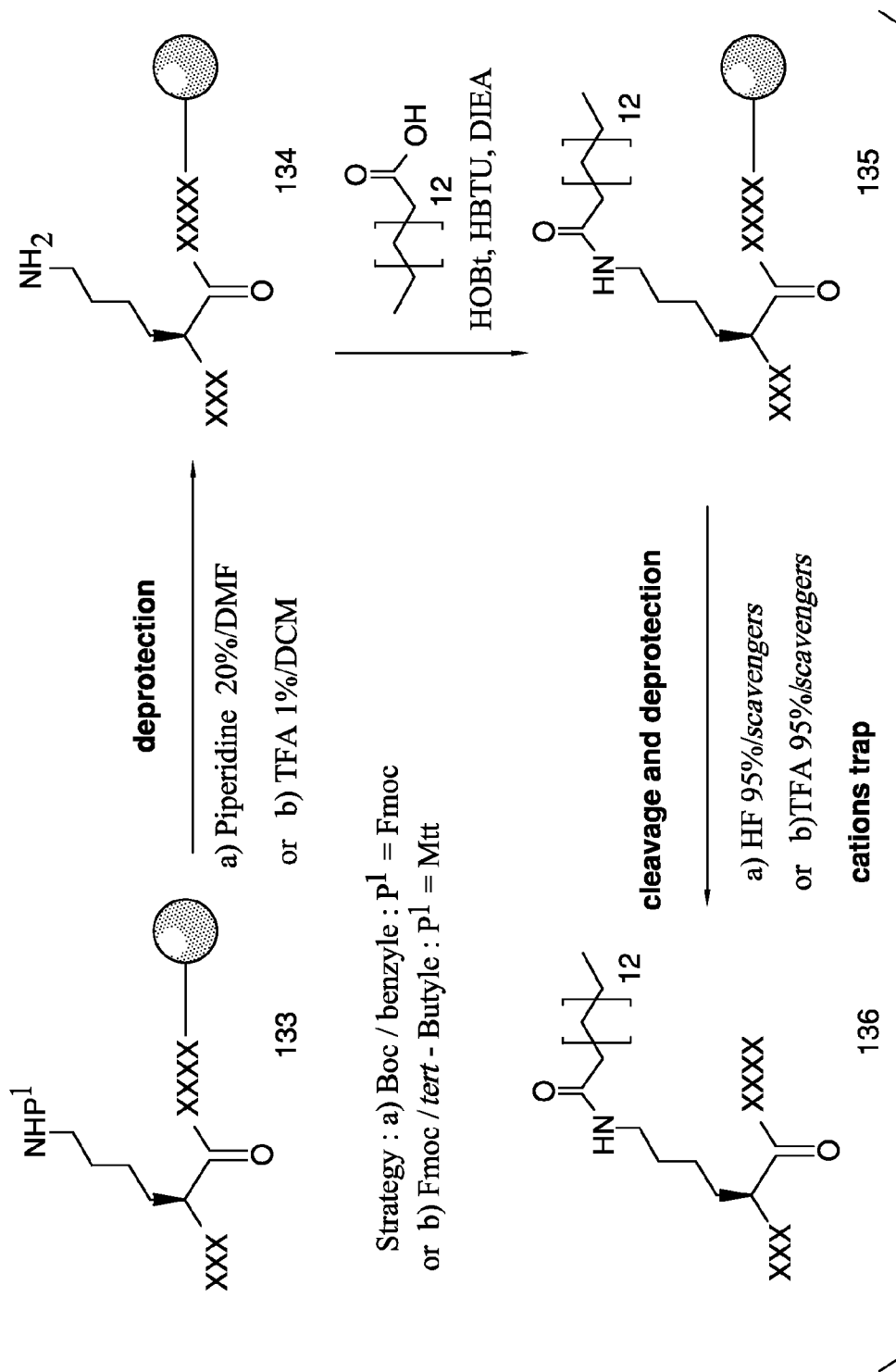
FIG. 2: Diagrammatic representation of the Boc/benzyl strategy for synthesizing the peptides on a solid support.

According to this method, the synthesis of the conjugates is based on the generation on resin of the desired peptide sequence, and then the deprotection of the amine functions of the N- and C-terminal lysines in order to couple them with the fatty acid containing a carbon chain of between C12 and C24. The final step is cleavage with anhydrous hydrofluoric acid. The conjugates were obtained using the Boc/benzyl strategy. The optimal approach consists in generating the peptide sequence on the solid phase and then in coupling an activated fatty acid to a selectively deprotected amine (or thiol) function. If the fatty acid is introduced at the N-terminal end, the peptide does not require any particular functional arrangements. On the other hand, introduction of the fatty acid in the C-terminal position is generally carried out on the ε-amino function of a lysine side chain. In the Boc/benzyl strategy, it is necessary to introduce the Boc-L-Lys(Fmoc)-OH amino acid during synthesis of the peptide. After having generated the entire sequence, the amino function is deprotected and then acylated with the fatty acid containing a carbon chain of between C12 and C24. The conjugate is finally deprotected and cleaved from the resin in the presence of a strong acid, anhydrous hydrofluoric acid (FIG. 2).

I-2 Evaluation of the Degree of Immunogenicity of the Peptides Coupled to Two or Four Fatty Acids Containing a Carbon Chain of Between C12 and C24

In order to further understand the degree of immunogenicity of the conjugates according to the invention, two types of conjugates were produced and tested. The first type of conjugate corresponds to the synthetic sequences of the peptides derived from the extracellular loops of the murine P-170 protein, covalently coupled to four molecules of fatty acid containing a carbon chain of between C12 and C24, per molecule of peptide. The second type of conjugate is made up of a peptide coupled only to two molecules of fatty acid. This study is illustrated by means of a specific example of dipalmitoylated and tetrapalmitoylated conjugates.

Table III describes the sequences of the di- and tetrapalmitoylated conjugates corresponding to loops 1, 2 and 4 of the murine P-170 protein and also their immunogenic capacity measured through the detection of antibodies by the Dot Blot technique and also the antibody titer by fluorescence units. It is observed that the mice which received liposomes containing conjugates with two palmityl residues do not show an immune response, with the exception of mpp'4, corresponding to loop 4 of the murine P-170 protein. The antibody titer induced by this conjugate is, however, four times lower than the titer induced by mpp4, i.e. the same sequence coupled to four palmityl residues. The mpp4 and mpp2 conjugates engender an immune response with an antibody titer in the region of 400 fluorescence units. In the context of the first peptide synthesis, no antibody was detected following injection of the mpp1 conjugate corresponding to the longest amino acid sequence, which could result from the peptide synthesis. In fact, the synthesis of this loop is very hard and long since there are many possible chemical terminations, or chemical rebridging which could explain the lack of immune response of this first batch of peptides. For the animal immunization trials, a further synthesis of the peptides, in particular of loop 1, was therefore carried out.

In view of these results, the model coupling each molecule of peptides to four molecules of fatty acid containing a carbon chain of between C12 and C24, strengthens the immunogenic capacity of said conjugates incorporated into the membrane of liposomes in the immunogenic composition according to the invention (FIG. 1). The tertiary structure induced by the hydrophobic interactions at the N and C terminal ends therefore plays a role in inducing a substantial and specific humoral immune response. These hydrophobic-type interactions are strong enough to create a loop conformation defined as being the equivalent tertiary structure of the natural structure of the extracellular loops of the P-170 protein. This "natural" conformation is stably exposed at the surface of the carrier, preferably at the surface of the liposomes, in the case of the conjugates coupled to four C12 to C24 fatty acid residues per molecule of peptides. A decrease in the hydrophobic interactions by a factor of two may be insufficient to obtain the "natural" structure resulting in an almost complete inhibition of the antigenic potential of the conjugates according to the invention.

TABLE III

| Conjugate name | Amino acid sequence | Number of palmityl chains | Detection of antibodies by Dot Blot | Ac titer fluorescence units |
|---|---|---|---|---|
| mpp1 (SEQ ID NO 1) | K-G-GNMTDSFTKAEASILPS ITNQSGPNSTLIISNSSLEEE- G-K-K-NH$_2$ | 4 | – | <10 |
| mpp'1a (SEQ ID NO 18) | G-GNMTDSFTKAEAS-G-K-NH2 | 2 | not tested | not tested |

TABLE III-continued

| Conjugate name | Amino acid sequence | Number of palmityl chains | Detection of antibodies by Dot Blot | Ac titer fluorescence units |
|---|---|---|---|---|
| mpp'1b (SEQ ID NO 19) | G-LPSITNQSGPNS-G-K-NH2 | 2 | − | <10 |
| mpp'1c (SEQ ID NO 20) | G-TLIISNSSLEEE-G-K-NH2 | 2 | − | <10 |
| mpp'2 (SEQ ID NO 21) | G-KVLTSFTNKELQAYAK-G-K-NH2 | 2 | − | <10 |
| mpp2 (SEQ ID NO 2) | K-G-KVLTSFTNKELQAYAK-G-K-K-NH2 | 4 | + | 360 |
| mpp'4 (SEQ ID NO 22) | G-SRDDDMETKRQNEN-G-K-NH2 | 2 | + | 100 |
| mpp4 (SEQ ID NO 3) | K-G-SRDDDMETKRQNEN-G-K-K-NH2 | 4 | + | 400 |

I-3 Vaccine Preparations

The immunogenic compositions prepared comprise:
Lp1: Conjugates, liposomes (DPMC, DPMG, cholesterol)
Lp2: Liposomes (DPMC, DPMG, cholesterol)
Lp3: Liposomes (DPMC, DPMG, cholesterol), MPLA, conjugates
Lp4: Conjugates.

The liposomes present at their surface the three conjugates mpp1, mpp2 and mpp3 added in a molar ratio of 1:250 with the phospholipids. The organic solvents allowing homogenization of this combination are evaporated off, and the resulting film, after hydration with sterile PBS pH=7.4, is adjusted to a final phospholipids concentration of 4 mM. Finally, the liposomes in suspension are, at the time of immunization, mixed with sterile alum (Pasteur Mérieux) in a ratio by volume. The vaccine preparations injected into the animals therefore correspond to the immunogenic compositions Lp1, Lp2, Lp3 and Lp4 in formulations comprising alum as adjuvant for immunity, the alum also being capable of prolonging the absorption time of the vaccine.

I-4 Animals

The studies were carried out on 6- to 10-week-old female B6D2F1 mice derived from crosses between C57B1/6 females and DBA/2 males (Charles River Laboratories). The mice used in the experiment weigh between 19 and 22 g. Blood samples are taken from the animal 7 to 12 days after immunization, from the retro-orbital sinus.

I-5 Immunization Protocol

The mice were immunized three times, two weeks apart, by intraperitoneal injection with 200 µl of vaccine composition. This experimental protocol is carried out for the four preparations on groups of nine B6D2 µl mice (Iffa Credo, L'Arbresle, France).

To quantify by Dot Blot the various immunoglobulins induced by the immunization, 100 µl of blood were taken, from each mouse, from the retroorbital sinus one day before the booster and 15 days after the final injection. Each blood sample was then centrifuged and the serum isolated was used for the quantification.

I-6 Anticancer Agents

Doxorubicin (Dox) (Sigma) and vinblastine (VLB) are used as anticancer agents in the protocol for the in vivo model of induction of solid tumors and of chemotherapy after immunization.

Doxorubicin is the leading cytostatic antineoplastic agent of the anthracycline family, it is therefore widely used alone or in combination in the treatment of many tumors. The main mode of action of doxorubicin appears to be on the inhibition of DNA topoisomerase II. However, like all anticancer medicinal products, doxorubicin has side effects, in particular of hematological, digestive and inflammatory type, and especially cardiac toxicity, which limits the use thereof in chemotherapeutic treatments. The doxorubicin solution is used at a concentration of $10^{-3}$ mol/l in the present experimentations.

Vinblastine is a vinca alkaloid commonly used in therapy as an agent for blocking cell mitoses in metaphase, hence its name of mitotic spindle poison. Vinblastine therefore preferentially cures rapidly dividing cells; it is therefore particularly suitable for the treatment of testicular cancer and Kaposi's sarcoma. However, there are many and varying toxic manifestations of vinblastine, the main one being blood toxicity. Finally, the vinblastine solution is used at a concentration of $10^{-2}$ mol/l in the experimental trials of the present invention.

I-7 In Vivo Model of Solid Tumor Induction

The B16R cell line, originating from a murine melanoma and selected for its resistance to doxorubicin, was chosen in the present invention for the development of solid tumors. The B16R cells are cultured in vitro, harvested in the exponential growth phase and cleaned with a phosphate buffer saline (PBS) before they are administered by subcutaneous injection into the rear flank of the mouse. The injection volume is 50 µl of a suspension of $1.10^6$ B16R cells in 0.85% NaCl (Candido K A et al. Cancer Res 2001, 61 (1):228-236). The mice develop a melanoma with an average size of 2.0 g±1.2 g within a period of between 22 and 24 days after inoculation of cancerous cells.

After tumor development, the B16R line was confirmed to be resistant to chemotherapeutic treatments with doxorubicin. Consequently, the preceding experimental conditions served as a model for inducing the solid tumor from murine P388R cells (murine lymphoid neoplasma cells characterized and used as reference cells for their MDR properties—Kohls W D. et al. Cancer Res 1986 September, 46(9): 4352-6), also resistant to doxorubicin.

Other tumor cells can be used provided that they exhibit resistance to the chemotherapy tested.

I-8 Protocol for Chemotherapy after Immunization

Figure 3:
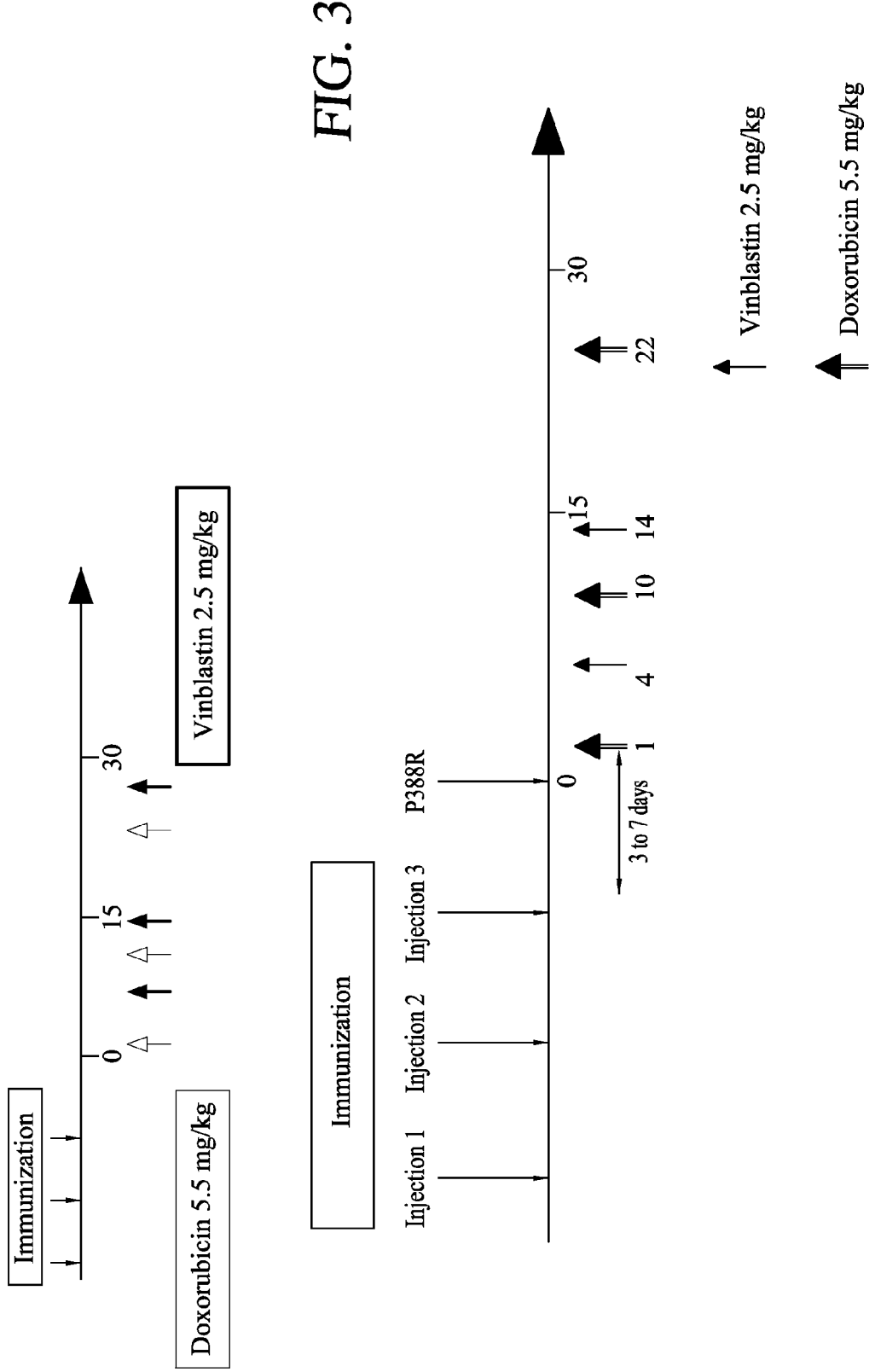
FIG. 3: Protocol for chemotherapy after immunization and injection of P388R cells in mice.

A protocol for chemotherapy using two anticancer agents, vinblastine and doxorubicin, was established as described in FIG. 3. The chemotherapeutic treatment of the mice pre-immunized with the vaccine preparations Lp1 and Lp2 begins one day after the subcutaneous injection of $10^6$ P388R cancer cells (day 0), by means of a weekly injection of doxorubicin at a dose of 5.5 mg/kg (days 1, 10 and 22) followed by the alternating injection of vinblastine at a dose of 2.5 mg/kg (days 4 and 14). During this period, the food intake, water intake and weight of the mice, and also their survival, were recorded. Before the injection with the P388R cells, samples of mouse serum were taken during a period for between 15 and 45 days after immunization, in order to quantify the anti-P170 antibodies and monitor their activity.

I-9 Analysis of the Immune Response by Dot Blot

The conjugates according to the invention serving as antigenic molecules, diluted in PBS, are firstly deposited at ambient temperature onto nitrocellulose membranes. After 30 minutes, these antigenic molecules are blocked with 3 ml of a solution containing PBS-5% skim milk. The membranes are incubated for 2 hours at ambient temperature, without washing, with 24 µl of murine serum prediluted volume-for-volume with PBS, in 2 ml of PBS containing 1% of skim milk and 0.1% of tween 20. Said murine serum was taken during a period of 15 to 45 days after the third immunization. After three washes in PBS-1% skim milk-0.1% tween 20, the membranes are sequentially incubated for 1 hour at ambient temperature, in 3 ml of PBS-1% skim milk-0.1% tween 20 containing the peroxydase anti-mouse secondary antibody diluted to 1/3000, and then after 2 washes, in 3 ml of PBS-1% skim milk-0.1% tween 20. The membranes are then washed once for 10 minutes in PBS alone and kept in a refrigerator at 4° C. overnight, in 500 µl of PBS. A chemoluminescence peroxydase substrate (ECL™ kit, AMERSHAM Pharmacie Biotech) is deposited at the surface of the membranes (0.125 ml/cm²), and left for one minute, and the membranes are then drained off and placed in a "cold" cassette between 2 films of Saran®. The membranes are immediately exposed by autoradiography, the emitted light resulting from the reaction of oxidation of the luminol by the peroxydase being collected on KODAK X-OMAT films with varying times from a few minutes to 1 hour, depending on the strength of the signal. The antibody titers are estimated using a densitometer suitable for the above system. The sensitivity of the chemoluminescence reaction has a threshold for detection of the induced antibodies evaluated at 0.2 ng/ml under the experimental conditions.

The protocols for the experiments to evaluate the immune response in vivo in the mice immunized with the vaccine preparations described above use anti-mpp1, mpp2 and mpp4 antibodies and also Ig (M, G3, G2a, G2b, G1) specific anti-murine secondary antibodies.

Figure 4:
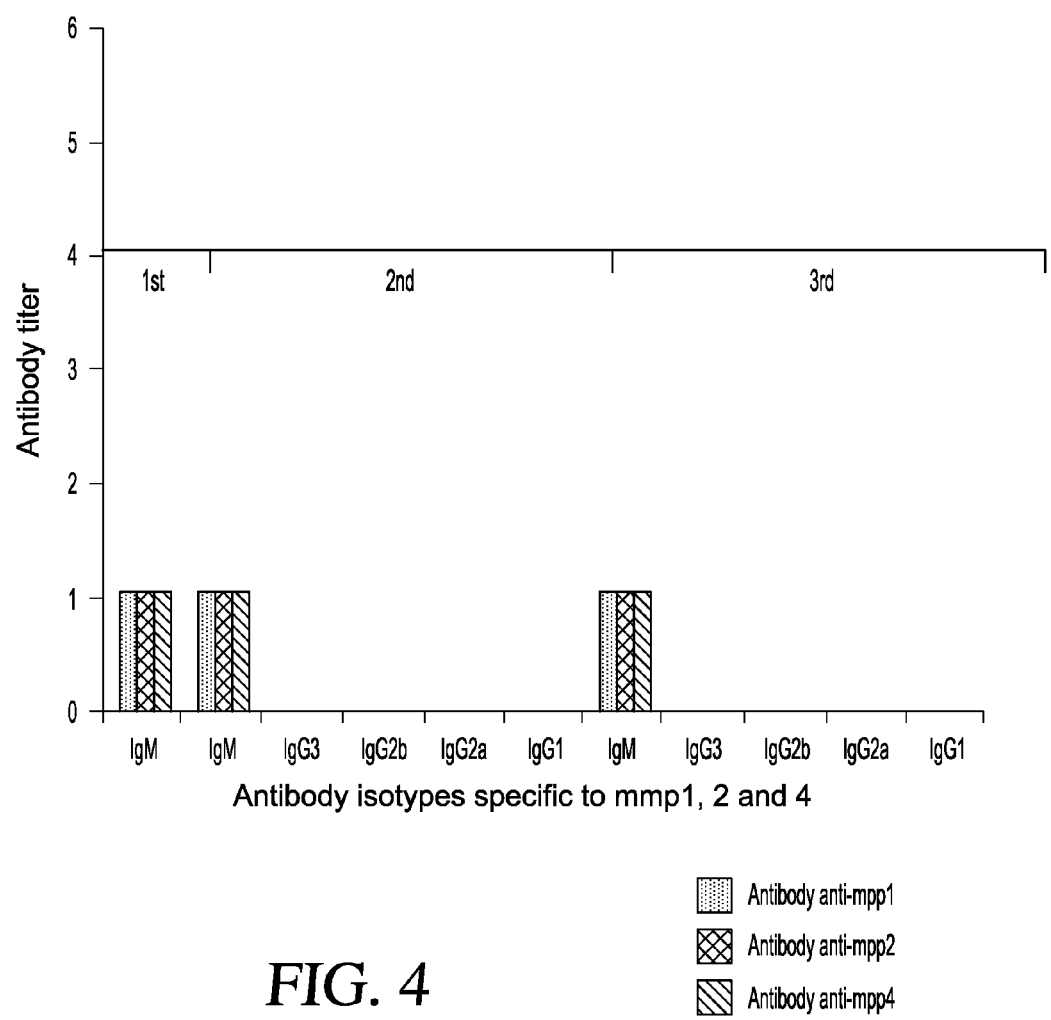
FIG. 4: Representation of the antibody titer as a function of the immunization time (1st, 2nd, 3rd injection) in the sera of mice immunized with Lp2. The anti-mpp1, mpp2 and mpp4 antibodies were quantified and the various isotypes were detected using Ig (M, G3, G2a, G2b, G1) specific anti-murine secondary antibodies, respectively. Each histogram represents the mean of the values obtained for 5 sera of mice bled 12 days after an immunization. One unit corresponds to 0.2 µg Ig/ml.

I-10 Immune Response In Vivo in the B6D2F1 Mice Immunized with the Vaccine Preparations The immune response of the B6D2F1 mice immunized with the control vaccine Lp2 shows predominantly IgM antibodies. The concentration of the IgM antibodies remains constant in the course of the three immunizations, reflecting an immune response of polyclonal aspecific type due to the presence of MPLA. The value for the IgM antibodies were subtracted from that found in the sera of mice immunized with the Lp1 vaccine (FIG. 4).

Figure 5:
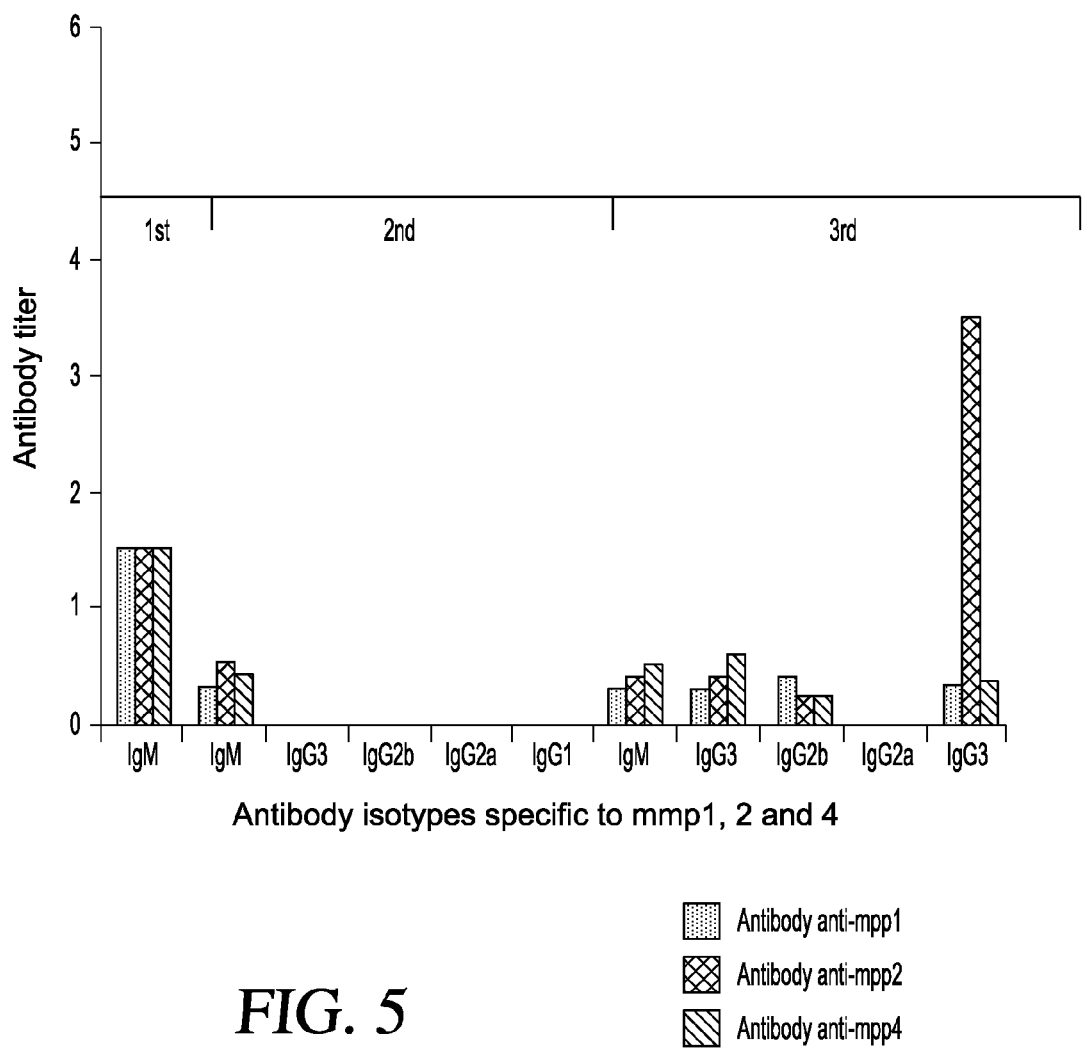
FIG. 5: Representation of the antibody titer as a function of the immunization time (1st, 2nd, 3rd injection) in the sera of mice immunized with Lp4. The anti-mpp1, mpp2 and mpp4 antibodies were quantified and the various isotypes were detected using Ig (M, G3, G2a, G2b, G1) specific anti-murine secondary antibodies, respectively. Each histogram represents the mean of the values obtained for 5 sera of mice bled 12 days after an immunization. One unit corresponds to 0.2 µg Ig/ml.

The mice immunized with the vaccine preparation Lp4 exhibit anti-mpp1, anti-mpp2 and anti-mpp3 IgM antibodies following the first immunization. This quantity of IgM antibodies decreases until it disappears following the third immunization so as to allow a predominantly IgG1 antibody immune response to emerge (FIG. 5).

Figure 6:
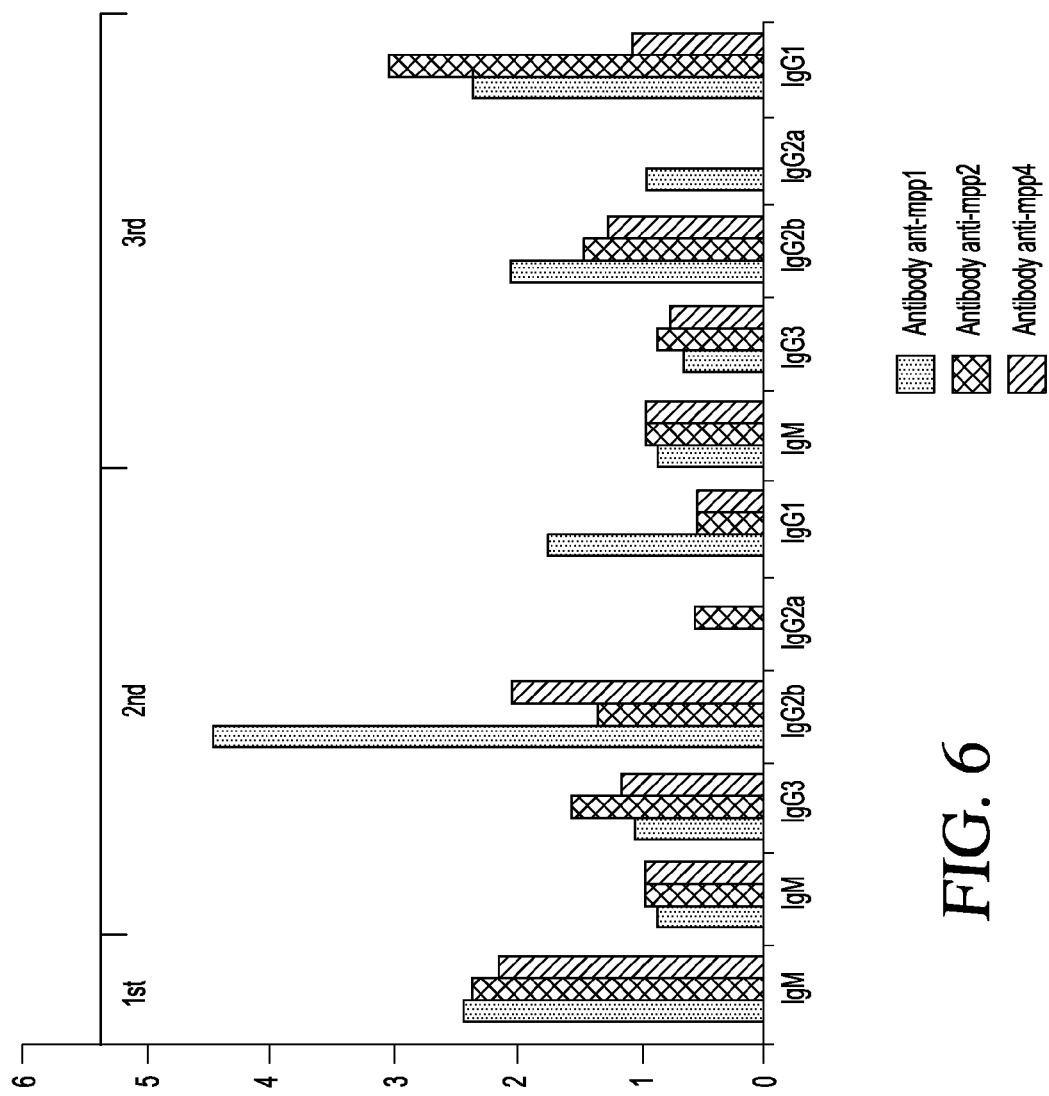
FIG. 6: Representation of the antibody titer as a function of the immunization time (1st, 2nd, 3rd injection) in the sera of mice immunized with Lp3. The anti-mpp1, mpp2 and mpp4 antibodies were quantified and the various isotypes were detected using Ig (M, G3, G2a, G2b, G1) specific anti-murine secondary antibodies, respectively. Each histogram represents the mean of the values obtained for 5 sera of mice bled 12 days after an immunization. One unit corresponds to 0.2 µg Ig/ml.

Immunization of the mice with the Lp3 vaccine induces the expression of IgM antibodies after the first injection. The IgM antibody titer decreases after the second immunization, during which period the immune response becomes predominantly an IgG2b antibody response. After the third injection, the IgG1 antibody titer is at a maximum; in addition, this immune response is positive for the three conjugates, the mpp2 conjugate being the most immunogenic (FIG. 6).

Figure 7:
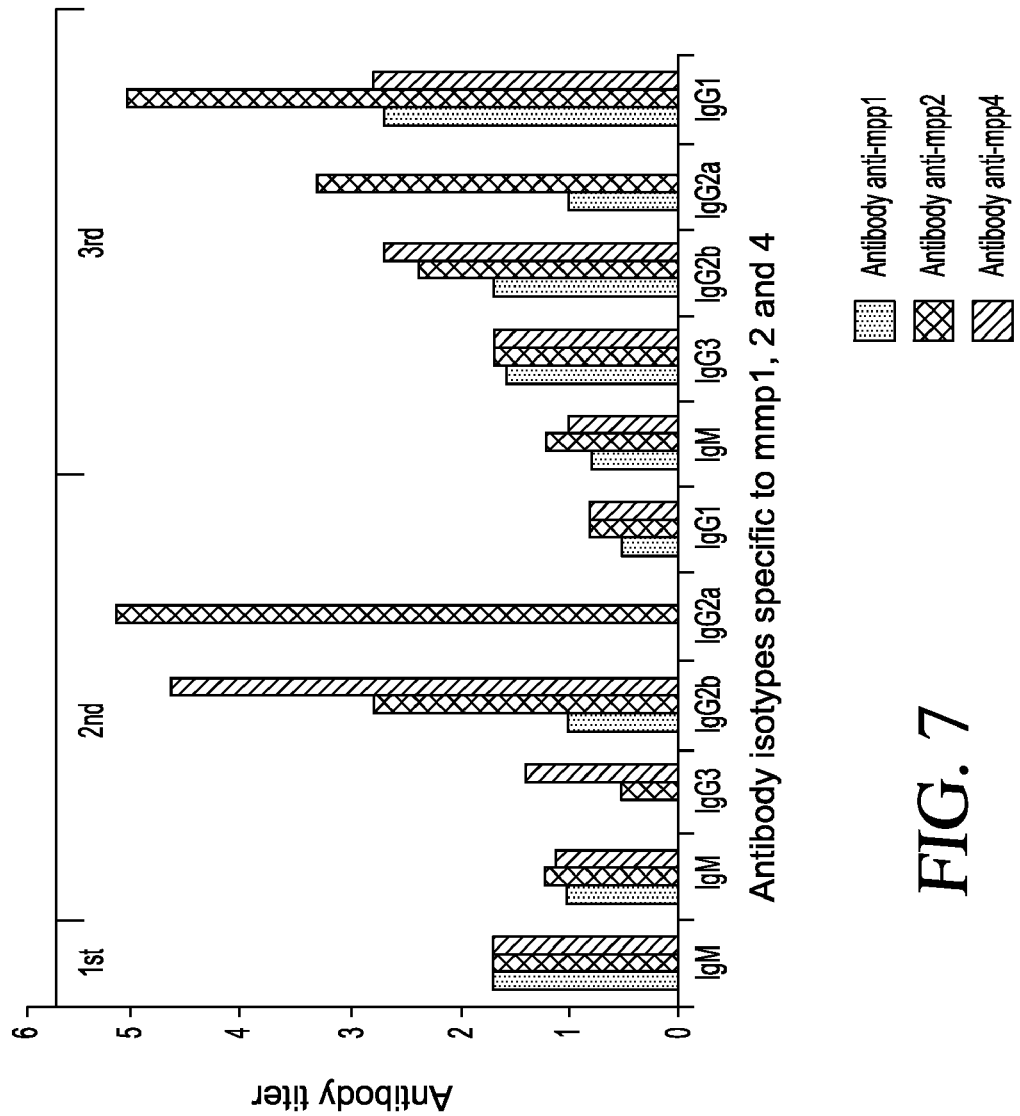
FIG. 7: Representation of the antibody titer as a function of the immunization time (1st, 2nd, 3rd injection) in the sera of mice immunized with Lp1. The anti-mpp1, mpp2 and mpp4 antibodies were quantified and the various isotypes were detected using Ig (M, G3, G2a, G2b, G1) specific anti-murine secondary antibodies, respectively. Each histogram represents the mean of the values obtained for 5 sera of mice bled 12 days after an immunization. One unit corresponds to 0.2 µg Ig/ml.

Immunization of the mice with the Lp1 vaccine preparation induces the predominant appearance of an IgM antibody directed against extracellular loops 1, 2 and 4 of the P-170 protein. The quantity of IgM antibody decreases in the course of the second and third immunizations, so as to allow a predominantly IgG anti-mpp2 antibody response to emerge. The IgG3, IgG2a and IgG2b antibody titers are approximately two to three times greater than the basal value, whereas the IgG1 antibody titer is five times greater (FIG. 7).

It is observed, by comparing the quantities of IgG1 antibodies, that the mpp2 conjugate is, respectively, 2.6 and 2 times more immunogenic than the mpp1 and mpp4 conjugates. In addition, it is noted that the Lp1 vaccine preparation induces the strongest overall immune response, i.e. the isotypes (IgM, G3, G2a, G2b, G1) corresponding to each of extracellular loops 1, 2 and 4 together.

The antibody titers induced by the mpp1 conjugate are significant and comparable in value to the antibody titers detected for the mpp2 and mpp4 conjugates, unlike the results observed with Tosi et al. (1995. Biochemical and biophysical research communications 212(2): 494-500).

After having determined that the Lp1 vaccine preparation had the best immunogenic capacity, its innocuity was checked over a period of 18 months after the final immunization. The mice immunized exhibit no significant variations in weight compared with the mice immunized with the Lp2 control vaccine. In addition, no behavioral modification, for example with regard to vigilance and appetite, was observed in the animals immunized with the Lp1 vaccine preparation. Finally, histopathological analyses of the organs naturally expressing the P-170 protein (spleen, liver, kidneys, adrenoglands, pancreas, ovaries, heart and lungs) demonstrated a lack of induced toxicity and/or of autoimmunity in the mice immunized with the Lp1 vaccine preparation. Specifically, the only lesions that could be observed in the intraperitoneal position or at the periphery of the organs (liver, pancreas, spleen and ovaries) were attributed exclusively to the use of alum in the immunogenic composition. Complementary analyses to investigate the agent inducing the lesions observed confirmed this result.

I-11 In Vivo Evaluation of the Anti-Chemoresistance Activity Associated with the Immunization with the Lp1 Vaccine Preparation The in vivo study of the evolution of the multidrug resistance phenotype in the mice immunized with the Lp1 and Lp2 (control) vaccine preparations was initiated according to a protocol of induction of solid tumors followed by the chemotherapeutic treatment plan. The anticancer treatment begins 1 day after inoculation of the cancer cells.

Prior to injection of the P 388R cells into the immunized mice, the antibody titers in the sera of the mice immunized with the Lp1 vaccine preparation were determined: 100%, 40% and 80%, respectively, of the sera exhibited anti-mpp1, 2 and 4 IgG1-type antibodies, with a mean value of 0.3, 0.21 and 0.33 µg/ml (1 U corresponds to 0.2 µg/ml).

Figure 8:
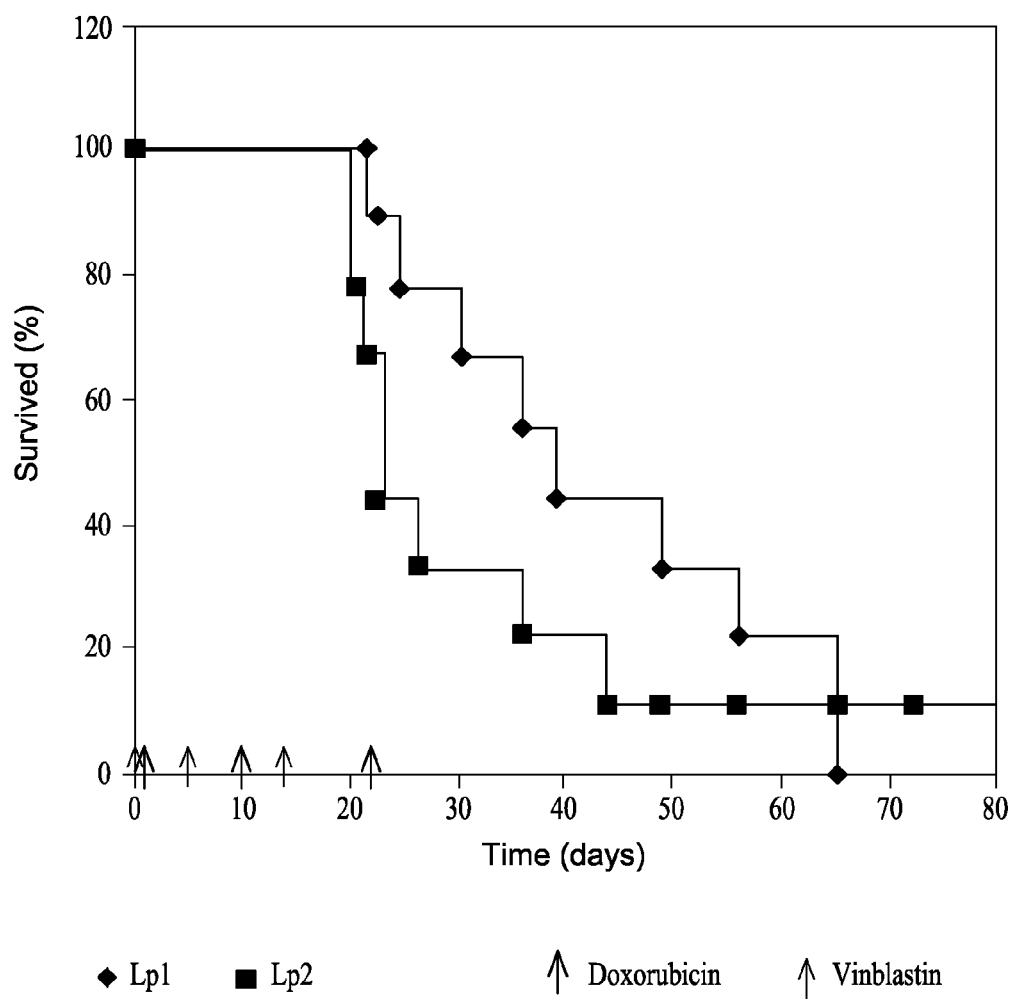
FIG. 8: survival time of the mice immunized with Lp1 and Lp2. At time 0, $10^6$ chemoresistant P388R cells were inoculated. On days 1, 10 and 22, 5.5 mg/kg of doxorubicin were injected and on days 4 and 14, 2.5 mg/kg of vinblastine were injected.

The survival time for the mice immunized with the Lp1 and Lp2 vaccine was represented as a function of time (FIG. 8).

The results represented by graph show that the mean survival time for the group of mice immunized with Lp1 is 39 days, whereas, in the group immunized with the Lp2 preparation, it is 22 days. The mice immunized with the Lp1 vaccine preparation in a preventive manner therefore exhibit a 77% increase in mean survival time compared with the control.

In the Lp2 group, a survival time of 70 days was observed for one of the mice.

This 77% increase in survival time is observed even though the chemotherapeutic treatment as such was only administered 22 days starting from the injection of the resistant cancer cells. Now, it is observed that the survival rate falls starting from the end of administration of the anticancer agents; consequently, it may be deduced therefrom that a complete reversion would be observed if the chemotherapeutic treatment continued, in the knowledge that only the latter has a curative effect, unlike the autoantibodies obtained in the patient immunized with the composition according to the present invention.

These results are very promising since the best published results obtained in the treatment of multidrug resistance with the same cancer model described a 49% increase in survival in mice treated with S9788 at doses of 100 mg/kg/day (Pierre et al. 1992. Invest New Drug. 10: 137-148). In addition, Yang et al. (1999. BBRC. 266: 167-173) observed, with the same cell line, a 35% increase in survival in mice treated with vincristine and cyclosporin A. Other authors have also demonstrated that certain reverting agents such as trans-flupenthixol can accelerate mortality by means of an increase in the invasive potential of the cancer cells.

This increase in survival time is all the more pleasing since the experimental murine cancer models are very demanding with respect to the effectiveness of the treatment, since, as soon as they are inoculated, the cancer cells have a degree of resistance that is greater than that observed clinically. This observation implies that the reversion agents are active as soon as the cancer cells are injected; now, it is noted that these agents are generally active at cytotoxic concentrations that are reached gradually during treatment.

Immunization with the Lp1 vaccine preparation induces in the mice the formation of active autoantibodies capable of rapidly, and in a long-lasting manner, inhibiting, in vivo, resistance to chemotherapy. Immunization with the Lp1 vaccine therefore makes it possible to rapidly inhibit chemoresistance and to reestablish in vivo the activity of anticancer agents in patients who have become refractory to the chemotherapeutic treatment. In the course of complementary experiments, the circulating autoantibodies in the mice immunized with the Lp1 preparation induced no cytotoxicity, no development of autoimmune lesions, nor any increase in the evasive potential of the cancer cells.

The above descriptions use in particular peptides of the murine P170 protein. The protocols described are, however, naturally applicable in a similar manner to the synthesis of any other peptide, in particular those which have been described above for the human P170 protein.

What is claimed is:

1. An composition comprising:
conjugates comprising at least one peptide consisting of between 10 and 25 amino acid residues, wherein the at least one peptide:
consists of SEQ ID NO: 5 or SEQ ID NO: 6,
comprises SEQ ID NO: 5 or SEQ ID NO: 6, or
consists of at least 10 consecutive amino acids of SEQ ID NO: 5 or SEQ ID NO: 6, each of said at least one peptide being combined with at least two molecules of fatty acid containing a carbon chain of between C12 and C24, and virosomes or liposomes.

2. The composition of claim 1, wherein said at least one peptide is selected from the group consisting of:
SEQ ID NO 5: GEMTDIFANAGNLEDLLMS,
SEQ ID NO 12: K-G-GEMTDIFANAGNLEDLLMS-G-K-K-$NH_2$,
SEQ ID NO 6: NITNRSDINDTGFF, and
SEQ ID NO 13: K-G-NITNRSDINDTGFF-G-K-K-$NH_2$.

3. The composition of claim 1, wherein each conjugate comprises four molecules of fatty acid containing a carbon chain of between C12 and C24.

4. The composition of claim 3, wherein the molecules of fatty acid are not provided in monounsaturated and/or polyunsaturated form.

5. The composition of claim 1, wherein the conjugates are tetrapalmitoylated.

6. The composition of claim 1 wherein said composition comprises liposomes.

7. The composition as claimed in claim 6, in which the conjugates and the liposomes are in a molar ratio of between 1/10 and 1/1000.

8. The composition of claim 6, wherein the liposomes are obtained by mixing the phospholipids dimyristoylphosphatidylcholine (DPMC), dimyristoylphosphatidylglycerol (DPMG) and cholesterol.

9. The composition as claimed in claim 8, in which the mixture of DPMC, DPMG and cholesterol is in the proportions 0.9:0.1:0.7.

10. The composition of claim 1 further comprising alum, calcium phosphate, interleukin 1, monophosphoryl lipid A (MPLA), microcapsules of proteins and of polysaccharides or combinations thereof.

11. The composition of claim 1 further comprising alum.

12. The composition of claim 7, wherein the conjugates and the liposomes are in a molar ratio of about 1/250.

13. The composition of claim 1, wherein said at least one peptide
consists of SEQ ID NO: 5,
comprises SEQ ID NO: 5, or
consists of at least 10 consecutive amino acids of SEQ ID NO: 5.

14. An isolated peptide derived from at least one extracellular loop of the P-170 protein and allowing induction of anti-P-170 antibodies, wherein said peptide consists of between 10 and 25 amino acid residues and comprises at least 10 consecutive amino acids of one of the following amino acid sequences:
SEQ ID NO 5, SEQ ID NO 6, SEQ ID NO 12, or SEQ ID NO 13.

15. A kit comprising the composition of claim 1 and, optionally, reagents and/or instructions for use.

16. A method for preparing the composition of claim 1, comprising:
a) synthesizing the amino acid sequences of the extracellular loops of the peptides of the conjugates on a solid support,
b) extending the peptides of the conjugates in the N- and/or C-terminal position with one or more amino acid residues so as to allow combination with fatty acid molecules,
c) deprotecting the amine functions of said N- and C-terminal amino acids in order to couple them with the fatty acids,
d) cleaving the conjugates synthesized on the solid support with a strong acid,
e) and, optionally, purifying the conjugates.

17. A method for preparing the composition of claim 1, comprising:
a) synthesizing the amino acid sequences of the extracellular loops of the peptides of the conjugates on a solid support;
b) deprotecting the amine functions of one or more internal amino acid residues in order to couple them with fatty acids,
c) combining said internal amino acid residues with fatty acid molecules, d) leaving the conjugates synthesized on the solid support with a strong acid, e) and, optionally, purifying the conjugates.

18. The method of claim 16, wherein the solid support is a resin.

19. The method of claim 16 further comprising presenting said conjugates at the surface of liposomes.

20. The method for preparing the composition of claim 17, wherein the solid support is a resin.

21. The method of claim 17 further comprising presenting said conjugates at the surface of liposomes.

* * * * *

UNITED STATES PATENT AND TRADEMARK OFFICE
CERTIFICATE OF CORRECTION

| | | |
|---|---|---|
| PATENT NO. | : 7,807,171 B2 | Page 1 of 1 |
| APPLICATION NO. | : 10/902276 | |
| DATED | : October 5, 2010 | |
| INVENTOR(S) | : Pierre-Francois Tosi et al. | |

It is certified that error appears in the above-identified patent and that said Letters Patent is hereby corrected as shown below:

Column 14, line 14, delete "Ig2" and insert --IgG2--.

Signed and Sealed this
Tenth Day of May, 2011

David J. Kappos
*Director of the United States Patent and Trademark Office*

SEQUENCE LISTING

<160> NUMBER OF SEQ ID NOS: 22

<210> SEQ ID NO 1
<211> LENGTH: 43
<212> TYPE: PRT
<213> ORGANISM: Mus musculus

<400> SEQUENCE: 1

Lys Gly Gly Asn Met Thr Asp Ser Phe Thr Lys Ala Glu Ala Ser Ile
1               5                   10                  15

Leu Pro Ser Ile Thr Asn Gln Ser Gly Pro Asn Ser Thr Leu Ile Ile
            20                  25                  30

Ser Asn Ser Ser Leu Glu Glu Glu Gly Lys Lys
        35                  40

<210> SEQ ID NO 2
<211> LENGTH: 21
<212> TYPE: PRT
<213> ORGANISM: Mus musculus

<400> SEQUENCE: 2

Lys Gly Lys Val Leu Thr Ser Phe Thr Asn Lys Glu Leu Gln Ala Tyr
1               5                   10                  15

Ala Lys Gly Lys Lys
            20

<210> SEQ ID NO 3
<211> LENGTH: 19
<212> TYPE: PRT
<213> ORGANISM: Mus musculus

<400> SEQUENCE: 3

Lys Gly Ser Arg Asp Asp Asp Met Glu Thr Lys Arg Gln Asn Glu Asn
1               5                   10                  15

Gly Lys Lys

<210> SEQ ID NO 4
<211> LENGTH: 48
<212> TYPE: PRT
<213> ORGANISM: Homo sapiens

<400> SEQUENCE: 4

Gly Glu Met Thr Asp Ile Phe Ala Asn Ala Gly Asn Leu Glu Asp Leu
1               5                   10                  15

Leu Met Ser Asn Ile Thr Asn Arg Ser Asp Ile Asn Asp Thr Gly Phe
                20                  25                  30

Phe Met Asn Leu Glu Glu Asp Met Thr Arg Tyr Ala Tyr Tyr Tyr Ser
            35                  40                  45

<210> SEQ ID NO 5
<211> LENGTH: 19
<212> TYPE: PRT
<213> ORGANISM: Homo sapiens

<400> SEQUENCE: 5

Gly Glu Met Thr Asp Ile Phe Ala Asn Ala Gly Asn Leu Glu Asp Leu
1               5                   10                  15

Leu Met Ser

<210> SEQ ID NO 6
<211> LENGTH: 14
<212> TYPE: PRT
<213> ORGANISM: Homo sapiens

<400> SEQUENCE: 6

Asn Ile Thr Asn Arg Ser Asp Ile Asn Asp Thr Gly Phe Phe
1               5                   10

<210> SEQ ID NO 7
<211> LENGTH: 15
<212> TYPE: PRT
<213> ORGANISM: Homo sapiens

<400> SEQUENCE: 7

Met Asn Leu Glu Glu Asp Met Thr Arg Tyr Ala Tyr Tyr Tyr Ser
1               5                   10                  15

<210> SEQ ID NO 8
<211> LENGTH: 25
<212> TYPE: PRT
<213> ORGANISM: Homo sapiens

<400> SEQUENCE: 8

Phe Ser Arg Ile Ile Gly Val Phe Thr Arg Ile Asp Asp Pro Glu Thr
1               5                   10                  15

Lys Arg Gln Asn Ser Asn Leu Phe Ser
                20                  25

<210> SEQ ID NO 9
<211> LENGTH: 18
<212> TYPE: PRT
<213> ORGANISM: Homo sapiens

<400> SEQUENCE: 9

```
Phe Thr Arg Ile Asp Asp Pro Glu Thr Lys Arg Gln Asn Ser Asn Leu
1               5                   10                  15

Phe Ser
```

<210> SEQ ID NO 10
<211> LENGTH: 17
<212> TYPE: PRT
<213> ORGANISM: Homo sapiens

<400> SEQUENCE: 10

```
Phe Arg Phe Gly Ala Tyr Leu Val Ala His Lys Leu Met Ser Phe Glu
1               5                   10                  15

Asp
```

<210> SEQ ID NO 11
<211> LENGTH: 53
<212> TYPE: PRT
<213> ORGANISM: Homo sapiens

<400> SEQUENCE: 11

```
Lys Gly Gly Glu Met Thr Asp Ile Phe Ala Asn Ala Gly Asn Leu Glu
1               5                   10                  15

Asp Leu Leu Met Ser Asn Ile Thr Asn Arg Ser Asp Ile Asn Asp Thr
            20                  25                  30

Gly Phe Phe Met Asn Leu Glu Glu Asp Met Thr Arg Tyr Ala Tyr Tyr
        35                  40                  45

Tyr Ser Gly Lys Lys
        50
```

<210> SEQ ID NO 12
<211> LENGTH: 24
<212> TYPE: PRT
<213> ORGANISM: Homo sapiens

<400> SEQUENCE: 12

```
Lys Gly Gly Glu Met Thr Asp Ile Phe Ala Asn Ala Gly Asn Leu Glu
1               5                   10                  15

Asp Leu Leu Met Ser Gly Lys Lys
            20
```

<210> SEQ ID NO 13
<211> LENGTH: 19
<212> TYPE: PRT
<213> ORGANISM: Homo sapiens

<400> SEQUENCE: 13

```
Lys Gly Asn Ile Thr Asn Arg Ser Asp Ile Asn Asp Thr Gly Phe Phe
1               5                   10                  15

Gly Lys Lys
```

<210> SEQ ID NO 14
<211> LENGTH: 20
<212> TYPE: PRT
<213> ORGANISM: Homo sapiens

<400> SEQUENCE: 14

```
Lys Gly Met Asn Leu Glu Glu Asp Met Thr Arg Tyr Ala Tyr Tyr Tyr
1               5                   10                  15

Ser Gly Lys Lys
        20
```

<210> SEQ ID NO 15
<211> LENGTH: 30
<212> TYPE: PRT
<213> ORGANISM: Homo sapiens

<400> SEQUENCE: 15

Lys Gly Phe Ser Arg Ile Ile Gly Val Phe Thr Arg Ile Asp Asp Pro
1               5                   10                  15

Glu Thr Lys Arg Gln Asn Ser Asn Leu Phe Ser Gly Lys Lys
            20                  25                  30

<210> SEQ ID NO 16
<211> LENGTH: 23
<212> TYPE: PRT
<213> ORGANISM: Homo sapiens

<400> SEQUENCE: 16

Lys Gly Phe Thr Arg Ile Asp Asp Pro Glu Thr Lys Arg Gln Asn Ser
1               5                   10                  15

Asn Leu Phe Ser Gly Lys Lys
            20

<210> SEQ ID NO 17
<211> LENGTH: 22
<212> TYPE: PRT
<213> ORGANISM: Homo sapiens

<400> SEQUENCE: 17

Lys Gly Phe Arg Phe Gly Ala Tyr Leu Val Ala His Lys Leu Met Ser
1               5                   10                  15

Phe Glu Asp Gly Lys Lys
            20

<210> SEQ ID NO 18
<211> LENGTH: 16
<212> TYPE: PRT
<213> ORGANISM: Mus musculus

<400> SEQUENCE: 18

Gly Gly Asn Met Thr Asp Ser Phe Thr Lys Ala Glu Ala Ser Gly Lys
1               5                   10                  15

<210> SEQ ID NO 19
<211> LENGTH: 15
<212> TYPE: PRT
<213> ORGANISM: Mus musculus

<400> SEQUENCE: 19

Gly Leu Pro Ser Ile Thr Asn Gln Ser Gly Pro Asn Ser Gly Lys
1               5                   10                  15

<210> SEQ ID NO 20
<211> LENGTH: 15
<212> TYPE: PRT
<213> ORGANISM: Mus musculus

<400> SEQUENCE: 20

Gly Thr Leu Ile Ile Ser Asn Ser Ser Leu Glu Glu Glu Gly Lys
1               5                   10                  15

<210> SEQ ID NO 21
<211> LENGTH: 19

```
-continued

<212> TYPE: PRT
<213> ORGANISM: Mus musculus

<400> SEQUENCE: 21

Gly Lys Val Leu Thr Ser Phe Thr Asn Lys Glu Leu Gln Ala Tyr Ala
1               5                   10                  15

Lys Gly Lys

<210> SEQ ID NO 22
<211> LENGTH: 17
<212> TYPE: PRT
<213> ORGANISM: Mus musculus

<400> SEQUENCE: 22

Gly Ser Arg Asp Asp Asp Met Glu Thr Lys Arg Gln Asn Glu Asn Gly
1               5                   10                  15

Lys
```